US008246917B2

(12) United States Patent  
Gracias et al.

(10) Patent No.: US 8,246,917 B2  
(45) Date of Patent: Aug. 21, 2012

(54) SELF-ASSEMBLED, MICROPATTERNED, AND RADIO FREQUENCY (RF) SHIELDED BIOCONTAINERS AND THEIR USES FOR REMOTE SPATIALLY CONTROLLED CHEMICAL DELIVERY

(75) Inventors: David H. Gracias, Baltimore, MD (US); Timothy Gar-Ming Leong, Alexandria, VA (US); Hongke Ye, Woburn, MA (US)

(73) Assignee: Johns Hopkins University, Baltimore, MD (US)

( * ) Notice: Subject to any disclaimer, the term of this patent is extended or adjusted under 35 U.S.C. 154(b) by 425 days.

(21) Appl. No.: 12/306,423

(22) PCT Filed: Jun. 25, 2007

(86) PCT No.: PCT/US2007/072029  
§ 371 (c)(1),  
(2), (4) Date: Jul. 28, 2009

(87) PCT Pub. No.: WO2008/108862  
PCT Pub. Date: Sep. 12, 2008

(65) Prior Publication Data  
US 2009/0311190 A1    Dec. 17, 2009

Related U.S. Application Data

(63) Continuation-in-part of application No. 11/491,829, filed on Jul. 24, 2006.

(60) Provisional application No. 60/816,063, filed on Jun. 23, 2006.

(51) Int. Cl.  
*B01L 3/00* (2006.01)

(52) U.S. Cl. ........ 422/547; 438/669; 977/700; 977/902; 977/904; 977/905; 977/906; 977/915

(58) Field of Classification Search ................... 422/547; 438/669; 977/700, 902, 904, 905, 906, 915  
See application file for complete search history.

(56) References Cited

U.S. PATENT DOCUMENTS

| | | | |
|---|---|---|---|
| 2,369,392 | A | 2/1965 | Ringer |
| 5,402,926 | A | 4/1995 | Takeuchi et al. |
| 5,688,486 | A | 11/1997 | Watson et al. |
| 6,432,253 | B1 | 8/2002 | Chung |
| 7,393,924 | B2 | 7/2008 | Vitaliano et al. |

(Continued)

OTHER PUBLICATIONS

Gracias et al. "Fabrication of Micrometer-Scale, Patterned Polyhedra by Self-Assembly", Advanced Materials (2002), 14, No. 3; Feb. 5, 2002; pp. 235-238.*

(Continued)

*Primary Examiner* — Brian J Sines  
(74) *Attorney, Agent, or Firm* — Ward and Smith, P.A.

(57) ABSTRACT

The present invention relates to a nanoscale or microscale particle for encapsulation and delivery of materials or substances, including, but not limited to, cells, drugs, tissue, gels and polymers contained within the particle, with subsequent release of the therapeutic materials in situ, methods of fabricating the particle by folding a 2D precursor into the 3D particle, and the use of the particle in in-vivo or in-vitro applications The particle can be in any polyhedral shape and its surfaces can have either no perforations or nano/microscale perforations The particle is coated with a biocompatible metal, e g gold, or polymer e g parvlene, layer and the surfaces and hinges of the particle are made of any metal or polymer combinations.

29 Claims, 24 Drawing Sheets

U.S. PATENT DOCUMENTS

| | | | |
|---|---|---|---|
| 2002/0119580 A1* | 8/2002 | Corless et al. | 436/518 |
| 2004/0028694 A1 | 2/2004 | Young et al. | |
| 2007/0004973 A1* | 1/2007 | Tan | 600/309 |
| 2007/0020310 A1 | 1/2007 | Gracias et al. | |
| 2007/0141163 A1 | 6/2007 | Vitaliano et al. | |
| 2007/0196281 A1* | 8/2007 | Jin et al. | 424/9.34 |
| 2007/0258889 A1* | 11/2007 | Douglas et al. | 424/1.37 |
| 2007/0258903 A1* | 11/2007 | Kleiner et al. | 424/9.3 |
| 2008/0103355 A1* | 5/2008 | Boyden et al. | 600/103 |
| 2009/0032592 A1* | 2/2009 | Christensen | 235/439 |
| 2009/0311190 A1 | 12/2009 | Gracias et al. | |

OTHER PUBLICATIONS

Bartels, L.W. et al., "MR Imaging of Vascular Stents: Effects of Susceptibility, Flow, and Radiofrequency Eddy Currents", J. Vasc Intery Radio, 2001: 12: 365-371.

Bennett, L.H., et al., "Artifacts in Magnetic Resonance Imaging from Metals", Journal of Applied Physics, 79 (8) 1996, 4712-4714.

Desai, T.A., et al., "Nanoporous Microsystems for Islet Cell Replacement", Advanced Drug Delivery Reviews, 56 (2004), 1661-1673.

Filipiak, et al., "Hierarchical Self-Assembly of Complex Polyhedral Microcontainers," J. Micromech. Microeng. 19 (2009).

Fireman, Z., et al., "Diagnosing Small Bowel Chrohn's Disease with Wireless Capsule Endoscopy", Gut (2003) 52, 390-392.

Ziaie, B., et al., Hard and Soft Micromachinging for BioMEMS: Review of Techiques and Examples of Applications in microfluidics and drug delivery, Advanced Drug Delivery Reviews 56 (2004) 145-172, 2003 Elsevier B.V.

Green, P.W., et al., "Demonstration of Three-Dimensional Microstructure Self-Assembly", Journal of Microelectromechanical Systems, vol. 4, No. 4, Dec. 1995, 170-176.

Harsh, K.F. et al., "Solder self-assembly for three-dimensinal microelectromechanical systems", Sensors and Actuators, 1999, vol. 77, pp. 237-244.

Hui, E.E., et al., "Single-step Assembly of Complex 3-D Microstructures", IEEE 13th International Conference on Micro Electro Mechanical Systems (2000), 602-607.

Kost, J. and Langer, R., "Responsive Polymeric Delivery Systems", Advanced Drug Delivery Reviews 46 (2001), 125-148.

Lanza, R.P., et al., "Encapsulated Cell Technology", Nature Biotechnology, V. 14, Sep. 14, 1996, 1107-1111.

Leoni, L., et al., "Micromachines Biocapsules for Cell-Based Sensing Delivery", Advanced Drug. Delivery Reviews 56 (2004) 211-229.

Leong, et al., "Surface Tension-Driven Self-Folding Polyhedra," Langmuir 23: 8747-8754 (2007).

Orive, G., et al., "Encapsulated Cell Technology: From Research to Market" Trends in Biotechnology, Sep. 20, 2002 (9): 382-387.

Santini, J.T., et al., "Microchips as Controlled Drug-Delivery Devices", Angew. Chem. Int. Ed. 2000, vol. 39, pp. 2396-2407.

Santini, J.T., et al., "A Controlled-Release Microchip", Nature, V. 397, Jan. 28, 1999, 335-338.

Schueler, B.A., et al., "MRI Compatibility and Visibility Assessment of Implantable Medical Devices", Journal of Magnetic Resonance Imaging (1999), vol. 9, pp. 596-603.

Shenhav, A., et al., "Gradient Field Switching as a Source for Artifacts in MR imaging of Metallic Stents", Magnetic Resonance in Medicine, 52: 1465-1468 (2004).

Simpson, N.E., et al., "NMR Properties of Alginate Microbeads", Biomaterials (2003) 24, 4941-4948.

Smela, E., et al., "Controlled Folding of Micrometer-Size Structures" Science v. 268, Jun. 23, 1995, 1735-1738.

Syms, R.R.A., et al., Surface Tension-Powered Self-Assembly for Microstructures—The State-of-the-Art, Journal of Microelectromechanical Systems, vol. 12, No. 4, Aug. 2003.

Thomlinson, R.H., et al., The Histological Structure of Some Human Lung Cancers and the Possible Implications for Radio-therapy, Dept. of Pathology, St. Thomas's Hospital, London and British Empire Cancer Campaign Research Unit, Sep. 22, 1955.

Rodney S. Ruoff, et al., "Single Crystal Metals Encapsulated in Carbon Nanoparticles", Science, vol. 259, Jan. 15, 1993, pp. 346-348.

* cited by examiner

SELF-ASSEMBLED, MICROPATTERNED, AND RADIO FREQUENCY (RF) SHIELDED BIOCONTAINERS AND THEIR USES FOR REMOTE SPATIALLY CONTROLLED CHEMICAL DELIVERY

CROSS-REFERENCE TO RELATED APPLICATIONS

This application is a 35 U.S.C. §371 U.S. national entry of International Application PCT/US2007/072029 having an international filing date of Jun. 25, 2007, which is a continuation-in-part of Ser. No. 11/491,829, filed on Jul. 24, 2006, which claims the benefit of U.S. Provisional Application No. 60/816,063, filed Jun. 23, 2006, and U.S. Provisional Application No. 60/701,903, filed Jul. 22, 2005, the content of each of the aforementioned applications is herein incorporated by reference in its entirety.

GOVERNMENT RIGHTS

This research was supported in part by the National Institutes of Health (NIH P50 CA 103175). The government of the United States may have rights to this invention.

FIELD OF THE INVENTION

The present invention relates to a microfabricated nano- or micro-scale particle for encapsulation and delivery of materials or substances including, but not limited to, biological media including cells, pharmaceutical agents, compositions, drugs, tissue, gels and polymers contained within the particle, with subsequent release of the therapeutic materials in situ, methods of making the particle and methods of using the particle in in vivo or in vitro applications.

BACKGROUND OF THE INVENTION

In recent years, advances in regenerative medicine have inspired therapies targeted at the cellular level. These therapies seek to implant cells or cellular clusters, manipulate cellular pathways, and target the delivery of drugs. For example, a wide range of cell lines have been enclosed within semipermeable and biocompatible immobilization devices that control the bidirection diffusion of molecules and cell release (R. P. Lanza, J. L. Hayes, W. L. Chick, Nat. Biotechnol. 14, 1107 (1996); G. Drive, R. M. Hernandez, A. R. Gascon, M. Igartua, J. L. Pedraz, J. L., Trends in Biotechnol. 20, 382 (2002) N. E. Simpson, S. C. Grant. S. J. Blackband, I. Constantinidis, Biomaterials 24, 4941 (2003)). Concurrent advances in microtechnology have revolutionized medicine, as new implantable devices, microarrays, biocapsules and microprobes are developed. These devices have facilitated cellular encapsulation, on-demand drug release, and early diagnosis of diseases (J. T. Santini, M. J. Cima, R. Langer, Nature 397, 335 (1999), J. Kost, R. Langer, Adv. Drug. Delivery Rev. 6, 19 (1991); L. Leoni, T. A. Desai, Adv. Drug Delivery Rev. 56, 211 (2004); B. Ziaie, A. Baldi. M. Lei, Y. Gu, R. A. Siegel, Adv. Drug Delivery Rev. 56, 145 (2004), T. A. Desai, T. West, M. Cohen, T. Boiarski, A. Rampersaud, Adv. Drug Delivery Rev. 56, 1661 (2004); J. T. Santini, A. C. Richards, R. Scheidt, M. J. Cima, R. Langer, Angew. Chem. 39, 2396 (2000), Z. Fireman, E. Mahajna, E. Broide, M. Shapiro, L. Fich, A. Sternberg, Y. Kopelman, E. Scapa, Gut 52, 390 (2003)). In contrast to polymeric, hydrogel, and sol-gel based processes that have been used for encapsulation and delivery, conventional silicon (Si) based microfabrication has high reproducibility, provides mechanical and chemical stability, and allows the incorporation of electronic and optical modules within the device, thereby facilitating wireless telemetry, remote activation and communication, in vivo. However, Si based microfabrication is inherently a two dimensional (2D) process and it is extremely difficult to fabricate three-dimensional (3D) systems using conventional microfabrication (M. Madou, Fundamentals of Microfabrication (CRC, Boca Raton, Fla. 1997)). A 3D medical device has several advantages over its 2D counterpart; (a) a larger external surface area to volume ratio, thereby maximizing interactions with the surrounding medium, and providing space to mount different diagnostic or delivery modules, (b) a finite volume allowing encapsulation of cells and drugs, and (c) a geometry that reduces the chances of the device being undesirably lodged in the body.

In one aspect of the present invention, biocontainers (i.e., boxes, hollow particles) have been fabricated by a strategy that combines the advantages of three-dimensionality with the desirable aspects of Si-based microfabrication to facilitate the delivery of therapeutic agents in situ. For example, the containers are loaded with microbeads or cells embedded in a gel and thus can be used either in conjunction with present day immobilization systems used in cell encapsulation technology, or they can be used independently. In another aspect, the biocontainers also can be used for encapsulation of functional cells within the porous containers for in vitro and in vivo release of therapeutic agents with or without immunosuppression. For example the containers can be used for encapsulation and delivery of insulin secreting cells for implantation in patients with diabetes for placing tumor innocula in animal models where constraining cells within a small region is necessary and for delivery of functional neuronal PC12 cells. In some embodiments, the faces of the container are patterned with microscale perforations allowing control over perfusion and release of its contents with the surrounding medium. The advantageous attributes of the containers are a parallel fabrication process with versatility in sizes and shapes; precise and monodisperse surface porosity; and the ability for remote guidance using magnetic fields. In another aspect, the containers of the present invention are easily detected and non-invasively tracked using conventional magnetic resonance imaging (MRI) and do not require the presence of a contrast agent.

SUMMARY OF THE INVENTION

The present invention provides nanoscale or microscale particles for encapsulation and delivery of materials or substances, including, but not limited to, cells, drugs, tissue, gels and polymers contained within the particle, with subsequent release of the therapeutic materials in situ, methods of fabricating the particle by folding a 2D precursor into the 3D particle, and the use of the particle in in-vivo or in-vitro applications. In one embodiment of the present invention, a three-dimensional particle comprises a multitude of two-dimensional forces that form a hollow, polyhedral shape and containing a fillable center chamber, wherein a size of the particle is microscale or nanoscale. In another embodiment, the two-dimensional faces of the particle are patterned with perforations or pores. In another embodiment, the perforations or pores are created photolithographically. In another embodiment, the perforations or pores have a size from about 0.1 nm to about 100 microns. In another embodiment, the particle is fabricated from at least one material selected from the group consisting of a metal, a polymer, a glass, a semiconductor, an insulator, and combinations thereof. In another embodiment, the metal is copper or nickel. In another embodiment, the particle is a Faraday cage. In another embodiment the particle is coated with a biocompatible material. In another embodiment, the biocompatible material is a metal, a polymer, or a combination thereof. In another embodiment, the fillable center chamber of the particle is filled with at least one substance comprising contents of the particle. In another embodiment, perforations or pores in the two-dimensional faces of the particle allow release of the contents of the particle. In another embodiment, at least one substance is a therapeutic agent. In another embodiment, the therapeutic agent is selected from the group consisting of a cell, a pharmaceutical agent, a composition a tissue, a gel, and a polymer. In another embodiment, the particle is administered to a subject and location of the particle in the subject is non-invasively tracked by magnetic resonance imaging. In another embodiment the particle is imaged with negative contrast relative to background or positive contrast relative to background.

The present invention also provides a method of fabricating a three-dimensional particle comprising a multitude of two-dimensional faces that form a hollow polyhedral shape and containing a fillable center chamber, the method comprising the steps: (a) fabricating a multitude of two dimensional faces; (b) patterning the fabricated two-dimensional faces; (c) patterning at least one hinge on the patterned two dimensional face to form a hinged edge; (d) joining a hinged edge of a first patterned two dimensional face to a hinged edge of a second patterned two dimensional face to form a hinged joint; (e) repeating step (d) to form a two dimensional precursor template having hinged joints between adjacent two dimensional faces; (f) liquefying the hinges of the two-dimensional template using heat; and (g) self-assembling the three-dimensional particle. In another embodiment, the hinges of step (c) of the method comprise a material that can be liquefied. In another embodiment, the material is a solder, a metallic alloy, a polymer or a glass. In another embodiment, step (a) of the method further comprises the steps (i) spinning a sacrificial film on a substrate to form a first layer; (ii) layering a conductive second layer on the first layer, and (iii) patterning the layered substrate by photolithography. In another embodiment the particle has a size that is microscale or nanoscale. In another embodiment, in step (b) of the method, the two-dimensional faces are patterned with perforations or pores. The perforations or pores are created photolithographically. In another embodiment, the perforations or pores have a size from about 0.1 nm to about 100 microns. In another embodiment, the particle is a Faraday cage.

The present invention further provides a method of imaging a three-dimensional particle comprising a multitude of two-dimensional faces that form a hollow polyhedral shape and containing a fillable center chamber that has been implanted into a subject, the method comprising the steps of: (i) loading the fillable center chamber of the particle with at least one substance to form a loaded particle; (ii) administering the loaded particle to the subject; and (iii) noninvasively tracking the particle of step (ii) in the subject by magnetic resonance imaging. In another embodiment, perforations or pores in the two-dimensional faces of the particle allow release of the substance in the fillable center chamber. In another embodiment, the at least one substance of step (i) is a therapeutic agent. In another embodiment, the therapeutic agent is selected from the group consisting of a cell, a pharmaceutical agent, a composition, a tissue, a gel, and a polymer.

BRIEF DESCRIPTION OF THE FIGURES

FIG. 1B-F are not drawn to scale in order to illustrate important dimensions.

DETAILED DESCRIPTION OF THE INVENTION

Figure 1:
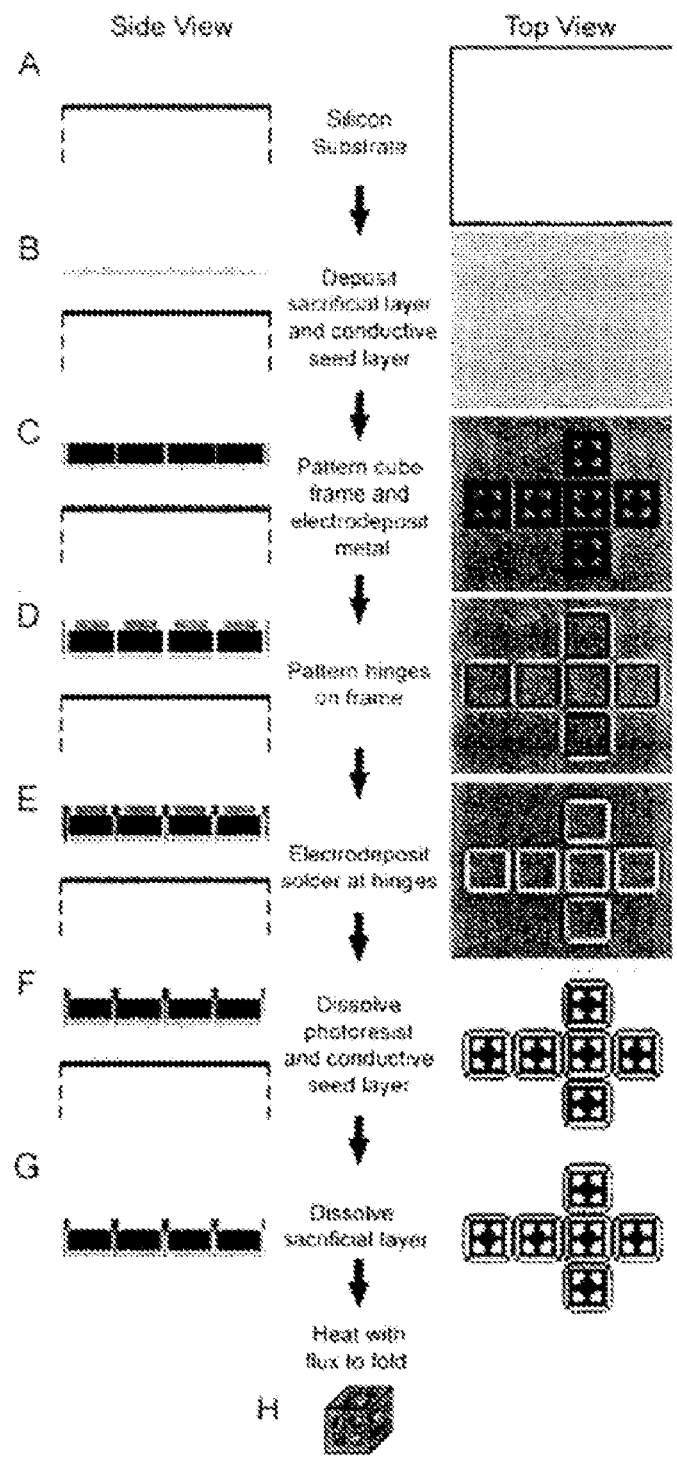
FIG. 1 is a schematic diagram of the process flow used to fabricate the 3D containers of the present invention.

The terms "particle," "hollow particle," "box," "container" and "biocontainer" are used interchangeably herein to mean a three-dimensional object, i.e., a receptacle, with a hollow interior or an interior capable of containing substances.

The term "colloid" or "colloidal" as used herein refers to a substance made up of a system of particles dispersed in a continuous medium.

Materials can react quite differently in the presence of an external magnetic field. Their reaction is dependent on a number of factors, including, but not limited to, the material's molecular structure, its atomic structure, and the net magnetic field associated with the atoms Most materials can be classified as ferromagnetic, diamagnetic, or paramagnetic.

The term "diamagnetic" as used herein refers to materials having a very weak form of magnetism exhibited only in the presence of an external magnetic field, which is the result of changes in the orbital motion of electrons due to the external magnetic field. The induced magnetic moment in a diamagnetic material is very small and in a direction opposite to that of the applied field. Examples of diamagnetic materials include, but are not limited to, copper, silver and gold.

The term "ferromagnetic" refers to materials having large and positive susceptibility to an external magnetic field. Ferromagnetic materials have some unpaired electrons so their atoms have a net magnetic moment. They exhibit a strong attraction to magnetic fields and are able to retain their magnetic properties after the external field has been removed. Examples of ferromagnetic materials include, but are not limited to, iron, nickel and cobalt.

The term "paramagnetic" refers to materials having a small and positive susceptibility to magnetic fields, which are slightly attracted by a magnetic field. Paramagnetic materials do not retain magnetic properties when the external field is removed. These paramagnetic properties are due to the presence of some unpaired electrons and the realignment of the electron orbits caused by the external magnetic field. Examples of paramagnetic materials include, but are not limited to, magnesium, molybdenum, and lithium.

The term "Faraday cage" as used herein refers to an enclosure designed to block the effects of an electric field, while allowing free passage to magnetic fields. (See E. M. Purcell, Electricity and Magnetism, Berkeley Physics Course Volume 2 (McGraw Hill, Mass., 1985)). Such an enclosure also is called a Faraday shield, Faraday shielding, Faraday screen, Faraday electrostatic shield, or shielded room.

The term "gel" as used herein refers to an apparently solid, jellylike material formed from a colloidal solution. By weight, gels are mostly liquid, yet they behave like solids. The term "solution" refers to a homogeneous mixture of one or more substances (the solutes) dissolved in another substance (the solvent).

The term "inductive heating" as used herein refers to the process of heating a metal object by electromagnetic induction, where eddy currents are generated within the metal and resistance leads to Joule heating of the metal. An induction heater (for any process) consists of an electromagnet, through which a high-frequency Alternating Current (AC) is passed. Heat may also be generated by magnetic hysteresis losses.

The term "magnetic field" as used herein refers to the region in space surrounding a magnetic body or entity, such as a permanent magnet or a conductor carrying a current, where an appreciable magnetic force is present. Such a field is represented by magnetic lines of force. In an electromagnetic field, for example, the magnetic field is perpendicular to the electrical field.

The term "magnetic field strength" or "magnetic field intensity" ("H") refers to the intensity of a magnetic field at a given point. Magnetic field strength is a vector quantity usually expressed in amperes per meter or in oersteds.

The term "magnetic resonance imaging: or "MRI", refers to a noninvasive imaging technique that uses the interaction between radio frequency pulses, a strong magnetic field, and an subject to construct images in slices/planes from the nuclear magnetic resonance (NMR) signal obtained from the hydrogen atoms inside the subject. The principle behind all MRI is the resonance equation, $$\nu = \gamma B_0 \quad \text{(Equation 1)}$$

which shows that the resonance frequency $\nu$ of a spin is proportional to the magnetic field $B_0$, it is experiencing, where $\gamma$ is the gyromagnetic ratio.

As used herein, the term "microscale" refers to particles that measure from about 1 μm or $1\times10^{-6}$ meters to about 999 μm in at least one dimension. As used herein the term "nanoscale" refers to particles that measure from about 1 nanometer or $1\times10^{-9}$ meters to about 999 nanometers.

The term "magnetic field gradient" refers to a variation in the magnetic field with respect to position. A one-dimensional magnetic field gradient is a variation with respect to one direction, while a two-dimensional gradient is a variation with respect to two directions. The most useful type of gradient in magnetic resonance imaging is a one-dimensional linear magnetic field gradient. A one-dimensional magnetic field gradient along, the x axis in a magnetic field, $B_0$, indicates that the magnetic field is increasing in the x direction. The symbols for a magnetic field gradient in the x, y, and z directions are $G_x$, $G_y$, and $G_z$.

In physics, the term "magnetic moment" or "dipole moment" refers to the pole strength of a magnetic source multiplied by the distance between the poles ($\mu$=pd), and is a measure of the strength of the magnetic source. The magnetic moment in a magnetic field is a measure of the magnetic flux set up by gyration of an electron charge in a magnetic field.

The term "micropattern" or "micropatterned" as used herein refers to any arbitrary two-dimensional pattern having microscale features. The term "nanopattern" or "nanopatterned" as used herein refers to any arbitrary two-dimensional pattern having microscale features. According to the present invention, the particles are patterned with perforations or pores ranging in size from about 0.1 nm to about 100 microns.

The term "oscillating magnetic field" or "oscillatory magnetic field" refers to a magnetic field that periodically increases and decreases its intensity, m, or which otherwise varies over time.

The particles of the present invention may be in any polyhedral shape. The term "polyhedral" as used herein refers to of or relating to or resembling a polyhedron. The term "polyhedron" refers to a three dimensional object bounded by plane polygons or faces. The term "polygon" refers to a multisided geometric figure that is bound by many straight lines, such as a triangle, a square, a pentagon, a hexagon, a heptagon, an octagon, and the like. For example, the particles of the present invention may be a cube or a tetrahedral.

The term "radio frequency" as used herein refers to a frequency or interval of frequencies within the electromagnetic spectrum used for communications, usually defined as spanning from about 3 kHz to about 300 GHz, which corresponds to wavelengths of about 100 km to about 1 mm respectively.

The term "radio frequency tag" as used herein includes radio frequency identification (RFID tags. Radio-frequency identification (RFID) is an automatic identification method, relying on storing and remotely retrieving data using devices called RFID tags. An RFID tag can be attached to or incorporated into an object for the purpose of identification using, radio waves. RFID tags come in three general varieties: passive, semi-passive (also known as battery-assisted), or active. Passive tags require no internal power source, whereas semi-passive and active tags require a power source, usually a small battery.

The term "resistance" refers to a measure of the degree to which an object opposes the passage of an electric current as represented by the equation, R=V/I, where R is the resistance of the object (usually measured in ohms, equivalent to J s/C$^2$); V is the potential difference across the object, usually measured in volts, and I is the current passing through the object, usually measured in amperes).

The presence of any substance in a magnetic field alters that field to some extent. The term "susceptibility effect" refers to the degree to which a substance's inherent magnetic moment produces polarization when placed in a magnetic field.

The terms "two-dimensional" or "2D" are used interchangeably herein to refer to a figure, object or area that has height and width, but no depth, and is therefore flat or planar.

The terms "three-dimensional" or "3D" are used interchangeably herein to refer to a figure, object or area that has height, width, and depth.

The particles of the present invention are fabricated using at least one material selected from the group consisting of a metal (meaning an element that is solid, has a metallic luster, is malleable and ductile, and conducts both heat and electricity), a polymer, a glass (meaning a brittle transparent solid with irregular atomic structure) a semiconductor (meaning an element, such as silicon, that is intermediate in electrical conductivity between conductors and insulators, through which conduction takes place by means of holes and electrons), and an insulator (meaning a material that is a poor conductor of heat energy and electricity). They were designed as miniature Faraday cages in order to facilitate detection in MRI. The particles shield (meaning protect, screen, block, absorb, avoid, or otherwise prevent the effects of) the oscillating magnetic fields in MM that arise from radio frequency (RF) and magnetic field gradients in an imaging sequence. This shielding occurs as a result of eddy currents (meaning circulating currents induced in a conductor moved through a magnetic field, or which is subjected to a varying magnetic field) generated in the frame of the particle that induce a local magnetic field, which interferes destructively with the external magnetic field.

In one aspect, the present invention describes the self-assembly of 3D metallic particles from 2D photolithographically or electrolithographically micropatterned precursors. The terms "photolithography", "photo-lithography." or "photolithographic process" refer to a lithographic technique in which precise patterns are created on substrates, such as metals or resins, through the use of photographically-produced masks. Typically, a substrate is coated with a photoresist film, which is dried or hardened, and then exposed through irradiation by light, such as ultraviolet light, shining through the photomask. The unprotected areas then are removed, usually through etching, which leaves the desired patterns. Electron beam lithography ma also be used to create the perforations or pores.

The particles of the present invention are self-folding and self-assembling. The at least one hinge of these structures comprises a material, including but not limited to, a solder (meaning an alloy formulated to have a specific melting point for use in joining metals), a metallic (meaning a mixture containing two or more metallic elements or metallic and nonmetallic elements usually fused together or dissolving into each other when molten), a polymer or a glass that can be liquefied. The surface tension of the liquid hinge provides the force necessary to fold the 2D template into the 3D particles.

In another aspect, after self-assembly, the fillable center chamber of the particles of the present invention is available as a vessel for encapsulation of therapeutic agents. As used herein, the term "therapeutic agent" refers to any pharmaceutical agent, composition, gene, protein cell, molecule, or substance that can be used to treat, control or prevent a disease, medical condition or disorder. The term "composition" refers to a mixture of ingredients. The term "pharmaceutical composition," as used herein, refers to a composition, which has under gone federal regulatory review. The term "treat" or "treating" includes abrogating, substantially inhibiting, slowing or reversing the progression of a condition, substantially ameliorating clinical or symptoms of a condition, and substantially preventing the appearance of clinical or symptoms of a condition. The amount of a therapeutic agent that result in a therapeutic or beneficial effect following its administration to a subject, including humans, is a "therapeutic amount" or "pharmaceutically effective amount". The therapeutic or beneficial effect can be curing, minimizing, preventing, or ameliorating a disease or disorder, or may have any other therapeutic or pharmaceutical beneficial effect. The term "disease" or "disorder," as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition," as used herein, refers to a variety of health states and is meant to include disorders, diseases, or injuries caused by any underlying mechanism or disorder, and includes the promotion of healthy tissues and organs.

In some embodiments, the fillable center chamber of the particles can be used to encapsulate such therapeutic agents as pharmaceutical agents or drugs, living tissue, gels and polymers, which subsequently are released in situ. As used herein, the term "polymer" refers to a natural, or synthetic compound consisting of long, repeated and sometimes branched chains, built Up from small subunits, called monomers. Natural polymers include proteins (polymer of amino acids) & cellulose (polymer of sugar molecules). There are mangy examples of synthetic polymers.

In some embodiments, functional cells (e.g., pancreatic islet cells, neuronal PC12 cells) can be encapsulated for in vitro and in vivo release with or without immunosuppression. Such particles can be administered to a subject in need thereof by microinjection, either as a single biocontainer or as a group of biocontainers and are useful for imaging, diagnostics, and therapeutics.

For example, in one embodiment, the interiors of a multitude of particles were filled with cells that were embedded in a gel. These cells could be released by immersing the biocontainer in an appropriate solvent. The magnetic resonance (MR) images of the particles embedded in fluidic media suggest RF shielding and a susceptibility effect, providing characteristic hypointensity (darkness) within the particle, thereby allowing the particles to be easily detected. This demonstration is the first step toward the design of 3D, micropatterned, non-invasively trackable, encapsulation and delivery devices.

The present invention provides a three-dimensional particle comprising a plurality of two-dimensional faces capable of self-folding, to form a hollow interior, wherein a size of the particle is microscale or nanoscale. The particle preferably ranges in size from 1 nm to 2 mm.

The particle further comprises at least one hinge, which may be comprised of any liquefiable material. For example, the hinge may be a polymer, a gel, glass or a metal.

The particle of the present invention has any shape, but preferably has surfaces forming a polyhedral shape, such as a cube. The particle's two-dimensional faces are patterned with perforations or pores. These perforations or pores may be created photolithographically, electrolithographically or using electron beam lithography. These perforations or pores have a size ranging from about 0.1 nm to about 1 cm. Preferably, these perforations or pores have a size from about 10 nm to about 1 cm.

The particle (container) of the present invention may be fabricated from any material, but preferably at least one material selected from the group consisting of a metal, a polymer a glass, a semiconductor, an insulator and combinations thereof. The particle may also comprise active electronic or semiconductor components such as transistors sensors, actuators, light emitting diodes, photodiodes and solar cells. If the particle is metal, such metal may be copper or nickel, In one embodiment, the particle is a Faraday cage. In another embodiment, the particle may be coated with a biocompatible material, such as a metal, a polymer, or a combination thereof. The particle may further be associated with a biosensor.

The particle may further comprise at least one substance, such as a therapeutic agent, encapsulated within the particle. The therapeutic agent may be a cell, a chemical or biological agent, a pharmaceutical agent, a composition, a tissue, a gel, and a polymer. In certain embodiments, perforations or pores in the two-dimensional faces of the particle allow release of the contents of the particle.

The particle of the present invention may be administered to a subject. In such an embodiment, the location of the particle in the subject may be non-invasively tracked by magnetic resonance imaging: or CAT scan (CT). The particle may be imaged with negative contrast relative to background or positive contrast relative to background.

In another embodiment of the invention, the particle additionally comprises a radio frequency tag, wherein the substance may be released upon the particle's exposure to a pre-selected frequency.

In a further embodiment of the particle of the invention, the substance may be released upon the particle's exposure to electromagnetic radiation, which may be triggered remotely. The electromagnetic radiation may range from 1 KHz to 1 Peta Hz.

In a further embodiment of the particle of the invention, the substance may be released upon the particle's exposure to inductive heating. Such inductive heating may be triggered remotely.

The present invention also provides a method of fabricating a three-dimensional particle comprising a multitude of two-dimensional faces that form a hollow polyhedral shape and containing a fillable center chamber. This method comprises the steps: (a) fabricating a multitude of two dimensional faces; (b) patterning the fabricated two-dimensional faces; (c) patterning at least one hinge on the patterned two dimensional face to form a hinged edge; (d) joining a hinged edge of a first patterned two dimensional face to a hinged edge of a second patterned two dimensional face to form a hinged joint; (e) repeating step (d) to form a two dimensional precursor template having hinged joints between adjacent two dimensional faces; and (f) liquefying the hinges of the two-dimensional template using heat to initiate self-folding. This method allows the particle to self-assemble.

In one embodiment of this method, the hinges of step (c) comprise a material that can be liquefied. The material may be a solder, a metallic alloy, a polymer or a glass.

In another embodiment of this method, step (a) further comprises the steps: (i) spinning a sacrificial film on a substrate to form a first layer; (ii) layering a conductive second layer on the first layer; and (iii) patterning the layered substrate by photolithography.

In these methods, the particle has a size that is microscale or nanoscale and may have two-dimensional faces patterned with perforations or pores, which may be created photolithographically and may vary in size from about 0.1 mm to about 100 microns. The particles of these methods may be a Faraday cage.

The invention further comprises a method of imaging a particle of the invention that has been implanted into a subject comprising the steps of (i) loading the hollow interior of the particle with at least one substance to form a loaded particle; (ii) administering the loaded particle to the subject; and (iii) non-invasively tracking the particle of step (ii) in the subject magnetic resonance imaging. In one embodiment, the particle has perforations or pores in its two-dimensional faces that allow release of the substance in the hollow interior. In one embodiment, at least one substance of step (i) is a therapeutic agent. The therapeutic agent may be a cell, a pharmaceutical agent, a composition, a tissue, and a polymer.

The methods of the invention also comprise a method of treating a condition comprising introducing into animal in need of treatment at least one particle of the invention encapsulating a composition, wherein the composition is released through one or more pores within the particle into the mammal in an amount sufficient to treat the condition. The pharmaceutical composition may be contained within one or more microbeads. In one embodiment of this method, the condition is diabetes, and the composition is one or more insulin-secreting cells.

The invention further provides a method for imaging a particle of the invention that has been introduced into a mammal comprises using magnetic resonance imaging.

The invention further provides a method for targeting the particle of claim 1 to a cell within a subject comprising the steps of: a) attaching to the particle an antibody against an antigen specific to the cell; and b) introducing the particle into the mammal, wherein the particle is targeted to the cell.

In another aspect, cells within or proximal to implanted particles of the present invention can be imaged by MRI to evaluate the efficacy of the implant and the condition of the encapsulated cells.

The inventions also provides a method of delivering one or more particles of the invention to a subject, wherein the particle is programmed to remotely release one or in more reagents at any specific time and at any specific spatial location. In one embodiment of this method, the particle is remotely guided and imaged using MRI or CT.

Also provided is a method of releasing a contrast agent from the particle of the invention or of providing contrast to allow MRI or CT imaging of its contents or of substances within its vicinity.

A method is also provided for conducting non-invasive biopsy or microsurgery, comprising directing the particles to a site within a subject using remote means, allowing the particle to capture one or more substances from the site, and obtaining the substance from the particle.

Where a range of values is provided, it is understood that each intervening value to the tenth of the unit of the lower limit unless the context clearly dictates otherwise, between the upper and lower limit of that range and any other stated or intervening value in that stated range is encompassed within the invention. The upper and lower limit of these smaller ranges, which may independently be included in the smaller ranges, is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing, of the present invention, the preferred methods and materials are now described. All publications mentioned therein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have We same meaning.

The publications discussed herein are provided solely for their disclosure prior to the tiling date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth to provide those of ordinary skill in the art with a complete disclosure and description of how to make and use the present invention, and are not intended to limit the scope of what the inventors regard as their invention nor they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are pans by weight, molecular weight is weight average molecular weight, temperature is in degrees Centigrade, and pressure is at or near atmospheric.

Example 1

Fabrication of the Containers (Particles)

FIG. 1 is a schematic diagram of the process flow used to fabricate the 3D containers of that present invention.

First, a 5 µm thick sacrificial layer of polymethyl methacrylate (PMMA, MW=996 K) was spun on a silicon substrate. The term "spinning," as used herein refers to a process whereby a fluid is dropped on a rotating substrate. A 15 nm layer of chromium (Cr) and a 100 nm thick layer of copper (Cu) were evaporated on top of the PMMA coated wafer. The Cr layer functions as an adhesive promoter while the Cu layer functions as a conductive seed layer for subsequent electrodeposition. Since it is necessary to etch the Cr and Cu later in the process, it is necessary to minimize their thickness to achieve a rapid etch. However, to minimize the electrical resistance of the film across the water during electrodepositton, the material thickness has to be increased. A thickness of 125 nm was deemed optimal for the present application. After thin film deposition, the substrate was patterned using photolithography. The photoresist Shipley SPR220 (Rohm and Haas, www.rohmhaas.com) was first spun on the wafer substrate, the thickness of the photoresist was controlled by changing the spin speed and the number of coats. After a soft bake, the resist was exposed to UV light using a mask aligner. The photomask used to pattern the resist was a transparency mask with six 200 nm squares spaced 20 pm apart. After exposure, the wafer was developed and the thickness of the resist was measured using Alpha-Step profilometer. Then, electrodeposition was used to build pattern the metallic faces of the container in the photoresist mold up to a height of 7-15 p.m, using commercial electrolytic solutions (Technic, Inc. www.technic.com) containing the metal ions of choice. (Cu was electrodeposited followed by a thin layer (about 1 pm) of gold (Au) to form non-magnetic containers and a thin layer (about 1 pm) of nickel (Ni) to fabricate magnetic containers. The Au was used to protect the Cu surface from subsequent etching steps and render it inert.

A second round of photolithography was performed in order to pattern the hinges. A second layer of SPR200 was spun on the substrate and a hinge photomask was used to pattern the hinges. The hinge mask consisted of two kinds of hinges (50×160 ($\mu m^2$ and 25×160 $\mu m^2$). The wider hinges were at the interfaces of adjacent faces while the narrower hinges were at the edges of the faces. Alignment marks were used to ensure perfect alignment of the hinges to the faces of the 2D precursor. Prior to hinge electrodeposition the exposed Cu and Cr in the area of the hinges were etched using commercial etchants (APS-110 for Cu and CRE-473 for Cr, Technic, Inc, www.technic.com). Although the etchants have a high selectivity of Cu or Cr with respect to Ni or Au, the etch time was optimized to minimize damage to the Ni or Cu/Au frame of the container. Pure tin (m.p. 232° C.) or tin/lead (Sn/Pb: m.p. 183° C.) solder was then electroplated in the hinge regions. The height of the hinges was approximately 5 µm to about 15 µm depending on the face pattern and the type of metal used (wetting or non-wetting). After electrodeposition, the original seed layer was etched and the 2D precursor template was immersed in a solution of N-Methyl Pyrrolidone (NMP, which dissolves the sacrificial PMMA layer) to release the precursors from the wafer. Approximately 50 precursors then were scattered in a small crystallizing dish using a pipette. A very thin layer of RMA-2 flux, (indium (Corporation, www.indium.com, used to dissolve any oxide formed on the solder) was poured into the dish. The dish was then heated to 100° C. for about 2 min to about 3 min and then ramped up to about 250° C. to about −300° C. for 20 seconds. Because of the low volume of flux, the agitation was sufficient to correct for defects in the folding but not large enough to cause the crosses to collide into each other and become fused. The molten solder generated the force needed to fold the 2D precursors into 3D containers. On cooling, the containers were permanently held together by solid solder hinges.

Diamagnetic copper (Cu) containers were fabricated with linear dimensions of about 200 pm (where one picometer is $10^{-2}$ meter). As compared to smaller or larger sized biocapsules, the 200 pm size provides the maximum encapsulation volume while still allowing the diffusion of oxygen and nutrients to the cells. It is known that if cells are more than about 150 μm to about 200 μm away from the nearest blood vessel, the environment becomes hypoxic (R. H. Thomlinson and L. H. Gray, Brit. J. Cancer Dec. 9, 539 (1995)). In principle the fabrication strategy described herein also would work on smaller or larger size scales in the design of containers for other applications. The linear dimension of the container was orders of magnitude smaller than the wavelength of the oscillating magnetic field at 500 MHz, which is the highest operating frequency in our magnetic resonance (MR) scanners. Hence, the size of the perforations on the faces of the container had no detrimental effect on the shielding characteristics of the container. The thickness of the faces of the container was designed to be larger than the conductor skin depth at the frequency of the radiation. The term "skin depth" refers to a measure of the average depth of penetration of an electromagnetic field into a material. It is defined as the depth at which the primary electromagnetic (EM) field is attenuated by/decreases to (1/e) of the field at the surface, or to approximately 37% of its value at the surface of the shield (A. Tsaliovich, *Electromagnetic Shielding Handbook for Wired and Wireless Applications* (Kluwer Academic Publishers, MA, 1999)). A thicker container also has lower conductor resistance, ensuring that the eddy currents persist long enough to maintain shielding during the time of image acquisition. The skin depth of Cu at 500 MHz is about 2.9 pm (C. Kittel, *Introduction to Solid State Physics*, (Wiley, New York, ed., at 7 (1995)); hence, containers were designed to have frames with thickness ranging from about 7 pm to about 15 pm.

Ferromagnetic nickel (Ni) containers in addition to the diamagnetic Cu containers described above were fabricated to investigate the effect of magnetic susceptibility on the MR images of the container. Magnetic field distortions including, but not limited to, shape, amplitude and phase distortions, resulting from the differences in magnetic susceptibility between an object and its surrounding medium cause a loss of phase coherence in the magnetization of the sample. Since the magnetic susceptibility of Cu is comparable to that of water, while that of Ni is orders of magnitude higher than that of water, a more pronounced distortion was expected for Ni containers in aqueous media (L. W. Bartels, et al., *J. Vasc. Interv. Radiol.* 12: 365 (2001)).

The strategy used to fabricate both the Cu and Ni containers involved the auto-folding of 2D metallic precursors using capillary forces. "Capillary action", "capillarity" or capillary motion, which are used interchangeably herein to refer to the ability of a narrow tube to draw a liquid upwards against the force of gravity, occurs when the adhesive intermolecular forces between the liquid and a solid are stronger than the cohesive intermolecular forces within the liquid. The same effect is what causes porous materials to soak up liquids. Previous demonstrations of auto-folding include the actuation of micrometer size components and the assembly of 3D complex structures (E. Smela, et al, *Science* 268: 1735 (1995); P. W. Breen et al., *J. Microelectromech. Syst.* 4: 170 (1995); K. F. Harsh et al., *Sens. Actuators A* 3: 237 (1999); E. E. Hui et al., *IEEEE 13th Int. Conf. On Micro Electro Mechanical Systems,* 602 (2000); D. H. Gracias, et al., *Adv. Mater.* 14: 235 (2002)).

According to one aspect of the present invention, 3D, hollow, perforated containers were fabricated from 2D precursors. The process used to fabricate the 2D precursors, which is an extension of the process described in Example 1, and required several additive layers, two photolithography steps, two electrodeposition steps, and a precise sequence of subtractive processes. Briefly, the process involved patterning the metallic 2D faces using photolithography and electrodeposition on top of a sacrificial layer. The versatility of the strategy was demonstrated by fabricating precursors whose faces contained two different patterns—one pattern comprised a square frame with open faces, while the other consisted of a microscale cross shaped pattern in the center of each face. In a second layer of photoresist, hinges were patterned on the edges of the frames. The width of the hinge between two adjacent faces was twice the width of the hinge at the edges so that all hinged joints had equal solder volume upon folding; the solder volume was critical to ensure a folding angle of 90° (R. R. A. Syms, et al., *J. Microelectromech. Syst.* 12: 387 (2003)) After the hinges were patterned, the 2D precursors were lifted off the wafer by dissolution of the sacrificial layer. The containers were self-assembled by heating the precursors above the melting point of the solder, wherein the liquid solder with high surface tension generated the force required to fold adjacent faces of the precursor.

Figure 2:
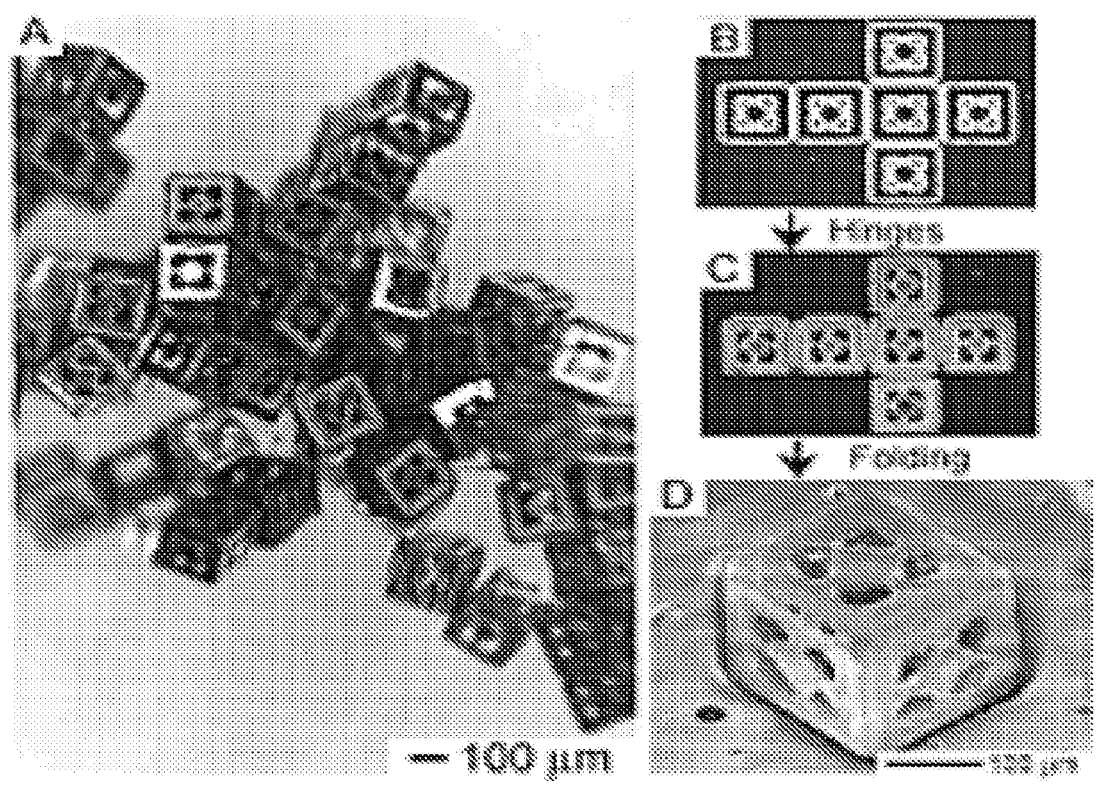
FIG. 2: (A) Optical image showing a collection of containers. (B-D) Optical and Scanning electron microscopy (SEM) images of micropatterned containers at different stages of the fabrication process; (B) the 2D precursor with electrodeposited faces, (C) the precursor with faces and hinges, and (D) the folded container.

FIG. 2A shows an optical image of a collection of containers that were fabricated using the process outlined above. The fabrication strategy allows a large number of containers to be constructed in a single process run. The primary yield-limiting factor was the error in estimating the volume of the solder to be electrodeposited at each hinge. The spacing between the adjacent faces was also critical—when the gap between faces was either too large or when the faces were fused, the yield of folding was greatly limited. FIG. 2B-2D show optical and SEM images of the micropatterned containers at different stages of the fabrication process: the 2D precursor with electrodeposited faces, the precursor with faces and hinges, and the folded container.

Although an open-faced container is not ideal for an encapsulation device, since it is considerably leaky, open-faced containers were filled for easy visualization of their contents. For in vivo applications it may be desirable to use the described strategy to construct containers with selectively sealed or micro/nano perforated faces, and fabricate more complex, polyhedral containers with rounded vertices. An open-faced container (FIG. 3A) was loaded with microbeads since many cellular delivery techniques use microbeads with cells adhered to their surface. In order to load the container with microbeads, a suspension of the beads in ethanol was pipetted onto the container. The suspension entered the container as a result of capillary forces. When the ethanol evaporated, the beads were held together by weak van der Waals forces (meaning the weak intermolecular forces that arise from the transient polarization of a given molecule into a dipole) (FIG. 3B); the glass beads could be released by agitation of the container.

Figure 3:
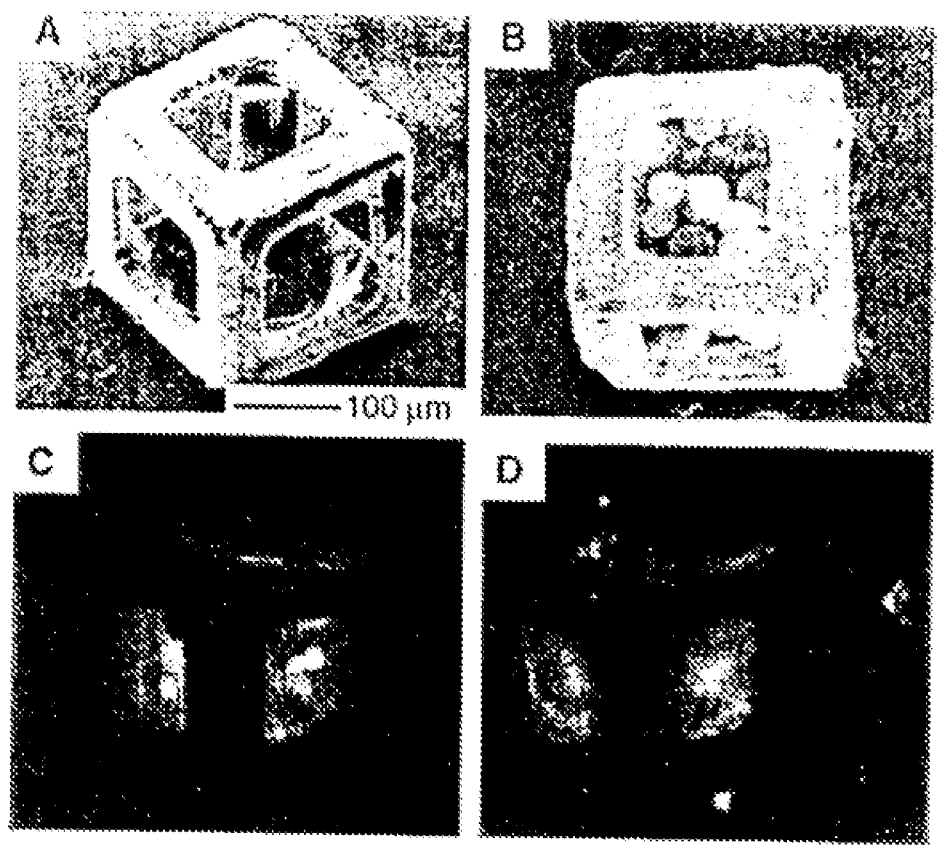
FIG. 3: (A) SEM image of a hollow, open-faced container. (B) SEM image of a container loaded with glass microbeads. (C) Optical image of a biocontainer loaded with MDAMB-231 breast cancer cells embedded than extra-cellular matrix (ECM) gel. (D) Release of the cells by immersion of the container in warm cell culture medium. (E) Optical image of a container loaded with a cell-ECM-agarose suspension stained with the fluorescent cell viability stain, Calcein-AM. (F) Release of the viable cells from the container on immersion in warm cell culture medium.

In order to demonstrate cellular encapsulation) MDA-MB-231 breast cancer cells in an extracellular matrix (ECM) suspension at 4° C. were loaded in the containers (FIG. 3C). As used herein, the term extracellular matrix refers to the complex structural entity surrounding and supporting cells that are found within mammalian tissues, as well as one or more of its constituents including, but not limited to, collagen, elastin, fibronectin and laminin. MDA-MB-231 cells are representative of rapidly proliferating cells and immortalized cells, such as βTC3 cells, used in diabetes therapy, and stem cells used in regeneration. On incubation at 37° C. for 5 min, the ECM suspension gelled; the cells were retained in the biocontainer and could be released by immersing the container in warm cell culture medium (FIG. 3D). It was also possible to load the biocontainers with a cell-ECM suspension within an agarose cavity. In this case, a suspension of 5% agarose gel was first micropipetted (60 µm tip) into the container using a stereotactic manipulator. The gel adhered to the sides of the container thereby sealing the faces and leaving a void in the center of the container. The cell-ECM suspension was then microinjected into this void, which was then sealed with a microdrop of agarose gel.

To demonstrate that the cells ere viable in the biocontainer and on release, the cells were stained with the fluorescent dye, Calcein-AM (Sigma-Aldrich), which stains positively for live cells. FIG. 3E shows calcein-stained cells within the biocontainer and FIG. 3F shows release of live cells from the container on immersion in warm cell culture medium. The frames of the biocontainers used in this demonstration had a thin gold or platinum coating on the interior faces for biocompatibility, since gold and platinum are inert or unreactive materials. Pure tin and tin/lead based solders were used to fold the containers. It may be necessary to use other solders containing inert metals such as silver and gold for enhanced biocompatibility. It is also possible to increase the biocompatibility of the containers, by coating the entire folded container with a layer of an inert metal (by electrodeposition) or with polymers (by immersion or vapor coating).

Figure 4:
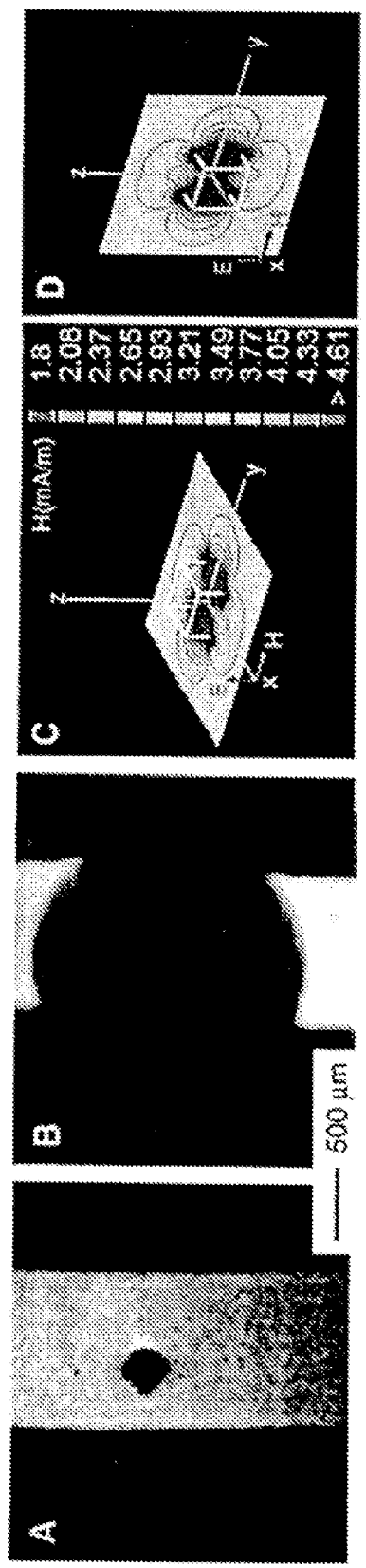
FIG. 4: MRI images of an open faced (A) non-magnetic CU container and (B) ferromagnetic Ni container. (C-D) Finite element simulation results of the near magnetic field in the region of a Cu container, in the (C) xy and (D) yz central planes. The excitation comprised a linear polarized 500 MHz plane wave of 1 V/m, with the E and H fields in the z and y direction respectively. The magnetic field distortions and the shielding effect caused by the wire frame are evident.

Non-invasive detection of the containers was demonstrated by embedding the containers in 5% agarose gel and imaging them with MRI in a 500 MHz vertical bore Bruker Avance microimaging system. For the images shown here, a 3D FLASH sequence with the echo time (TE) in the range of 4-6 ms, a repetition time (TR) of 50 ms, flip-angle of 30°, and a spatial resolution of 25 µm×25 µm×20 µm was used. The containers also were imaged using a standard spin echo sequence (meaning a pulse sequence used in magnetic resonance imaging based on the detection of a spin or Hahn echo, which uses 90° radiofrequency pulses to excite the magnetism and one or more 180° pulses to refocus the spins to generate signal echoes named "spin echoes"), with similar results. FIG. 4 shows MR images of a 900 µm diameter capillary containing a Cu (FIG. 4A) and a Ni (FIG. 4B) container embedded in agarose gel. A characteristic signature was observed for both the Cu and the Ni containers—there is a pronounced darkness in the of each container. These hypointense (dark) signatures have been observed before in MRI of larger centimeter scale metallic coils (A. Shenhav, H. Azhari, *Magn. Reson. Med.* 52: 1465 (2004)). While the region of hypointensity (darkness) in the MR image was comparable to the size of the non-magnetic Cu container, it was much larger for the ferromagnetic Ni container due to a pronounced susceptibility effect (L. H. Bennett, et al., *J. Appl. Phys.* 79: 4712 (1996): B. A. Schueler, et al., *J. Magn. Reson. Imaging* 9: 596 (1999)). The images of containers made of a given material were similar for both open faced containers as well as cross faced containers, showing that the pattern of the faces had little bearing on the MR signature at this size scale.

RF shielding was simulated in a non-magnetic container with a finite element model for a 200 gm scale wire frame that was excited by a linear polarized electromagnetic wave. FIG. 4C-4D are simulation results showing magnetic field distortions in the vicinity of the container and reduced field magnitude in the interior of the container.

Figure 5:
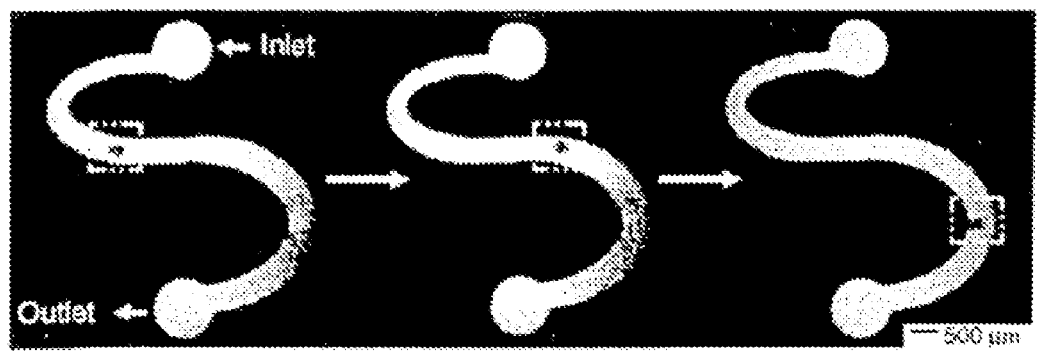
FIG. 5: MR tracking of a container in a fluidic channel. MR images of the container at different time points taken under pressure driven flow of the fluid.

For many biomedical applications it is necessary to non-invasively track an encapsulation device. The Cu container of the present invention could be tracked spatially and temporally with MRI in flow through an S-shaped 500 pm diameter fluidic channel. The channel was fabricated by molding poly dimethyl siloxane (PDMS) in an SU-8 photoresist mold that was patterned using photolithography. The channel was sealed with a second, flat, oxygen plasma treated PDMS layer. Polyethylene tubes were connected to the inlet and outlet ports of the channel, the channel was flushed with silicone oil, and the container was introduced into the channel. Under pressure driven flow, the container moved within the channel and was imaged at different positions; the sequence of MRI images is shown in FIG. 5. This ready trackability with MRI at very short echo times, without the need for a contrast agent, highlights a major advantage of the 3D metallic biocontainers of the present invention as compared to many other encapsulation systems.

Example 2

Simulation of Near Magnetic Fields in the Region of the Container

To demonstrate an RF shielding effect, the near magnetic field response in the vicinity of the container was simulated using a finite element electromagnetic simulation package, FEKO (EM Software & Systems-SA Ltd., www.feko.Info/). A full-wave method of moments approach was used to simulate the near magnetic field in the region of a 200 µm wire frame with wire segments of 8 µm radius, assuming perfect electric conductors coated with copper (conductivity=$5.813 \times 10^7$ S·m$^{-1}$). The simulation of the cubical wire frame model was performed with a linear polarized plane wave excitation at 500 MHz; we used an excitation source of 1 V/m incident on the wire frame, with E in the z direction and H in the y direction (FIG. 4C). The copper wire frame was assigned a relative permeability of 1, thereby simulating only the RF shielding effect and not the susceptibility effects. FIG. 4C shows the near magnetic field response it both the x-y and the y-z central planes.

In conclusion, the described strategy can be used to fabricate 3D, arbitrarily micropatternable, non-invasively trackable biocontainers that allow perfusion between the contents of the biocontainers and the surrounding medium. These biocontainers are encapsulation devices that do not lose their detectability when loaded with biological content. Due to their strength and high porosity, such metallic biocontainers are useful as basic elements of a scaffold to guide the growth of cells in 3D. Since the fabrication strategy described here is compatible with conventional 2D microfabrication, it also may be possible to add electromechanical modules for remote activation, wireless communication, signal processing, and biosensing to the faces of the biocontainers, to enable medical diagnostics and therapeutics. The present invention also envisions that such 3D containers, which function as small Faraday cages, will find utility in other applications requiring electromagnetic shielding in small volumes.

Example 3

Microfabrication and Self-Assembly of 3d Microboxes for Biomedical Applications

Figure 6:
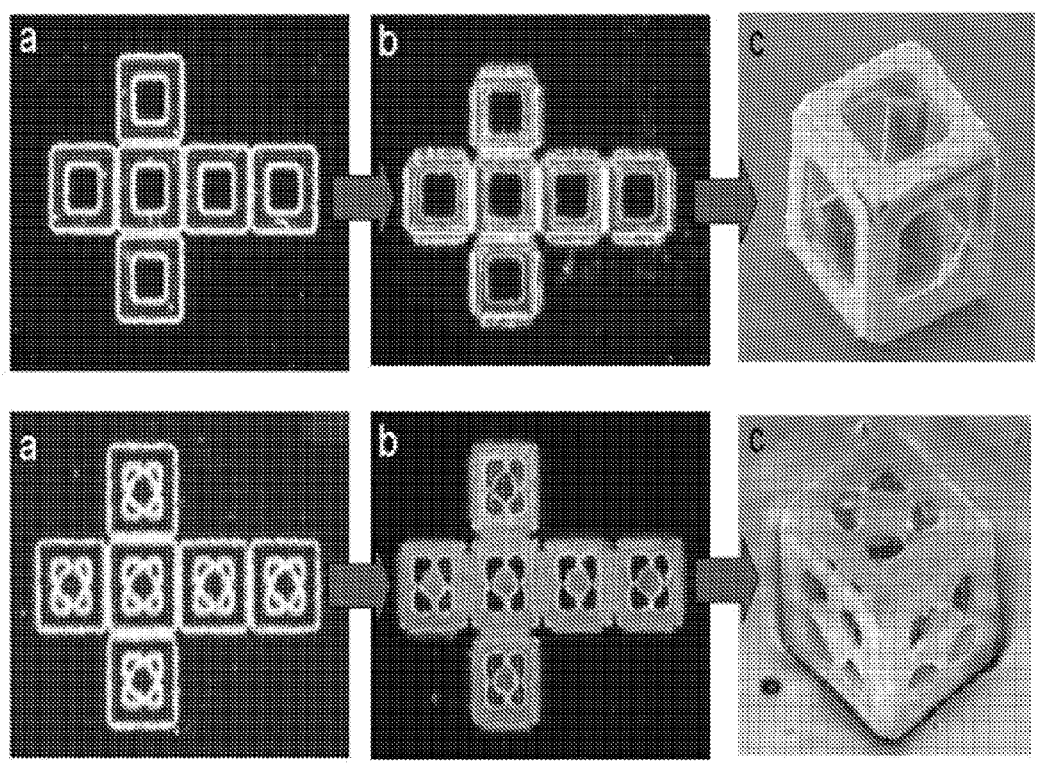
FIG. 6: Optical and SEM images of the three steps used to fabricate micropatterned boxes. The boxes shown have approximate dimensions of 200 microns. From left to right: (a) The faces were patterned using photolithography and electrodeposition; (b) Solder hinges were aligned relative to the faces using photolithography etching and electrodeposition; and (c) the 2D precursor was lifted off the wafer upon dissolution of a sacrificial layer. When the 2D precursor was heated above the melting point of the solder, the structure folded into a 3D cubic box [B. Gimi et al. *Biomed. Microdevices*, vol. 7, p. 341-345, 2006].

Experimental Methods and Results:
Fabrication:

The process used to fabricate the boxes consists of microfabrication and surface tension driven self-assembly [K. F. Harsh, V. M. Bright, & Y. C. lee, *Sens. Actuators A*, vol. 77, 237-244, 1999; E. E. Hui, R. T. Howe, & M. S. Rodgers, in *IEEE 13th Int. Conf. on Microelectromechanical Sys.*, 2002, pp. 602-607; R. R. A. Syms, E. M. Yeatman, V. M. Bright, & G. M. Whitesides, *J. Microelectromechanical Sys.*, vol. 12, pp. 387-417, 2003] to fabricate and fold a 2D precursor into a 3D hollow structure. The fabrication process involved three steps: (1) patterning the faces on the 2D precursor (2) patterning solder hinges between the faces, and (3) self-assembly of the 2D precursor (FIG. 6) The boxes self-assembled when the precursors were heated above the melting point of the solder, wherein the liquid solder with high surface tension generated the force required to assemble adjacent surfaces. The fabrication strategy allows a large number of boxes to be constructed in a single process run. Copper (Cu) and nickel (Ni) boxes have been fabricated with and without gold (Au) coated surfaces (to increase bioinertness).

Figure 7:
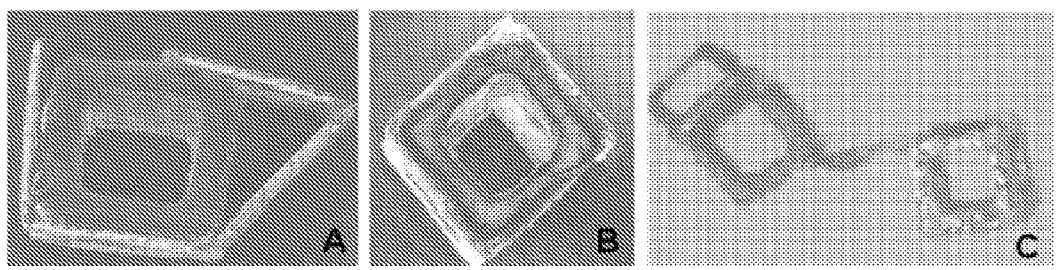
FIG. 7: Images of some defect modes observed: If the solder height is not optimized (A) underfolded or (B) overfolded boxes are observed. (C) Incomplete etching of the seed layer usually results in faces that cannot fold (180°), because they are fused together with the seed layer.

Defect Modes:

Several defect modes were observed (FIG. 7); however when the process was optimized yields as high as 90% flow from a single wafer were obtained. A part from obvious defect modes such as over electrodeposition that merges the faces, misalignment of the hinges with respect to the faces, and over or under etching of the seed layer, the largest defect limiter was the height of solder electrodeposited at the hinges. If too much or too little solder is electrodeposited the structure over or under folds. In order to determine optimum solder height for 90° folding, published design rules [R. R. A. Syms, E. M. Yeatman, V. M. Bright, & G. M. Whitesides, *J. Microelectromechanical Sys.*, vol. 12, pp. 387-417, 2003] were used. Additionally, in order to increase the error tolerance, hinges were designed between adjacent faces to be twice the width of lateral solder regions patterned along the edges of the faces. During electrodeposition, due to the elevated temperature (200° C.) the precursors were agitated (due to convective flow in the fluid in which the boxes were self-assembled); this agitation aided in correcting metastable minima (errors) and helped the box fold to the thermodynamic minimum.

Figure 8:
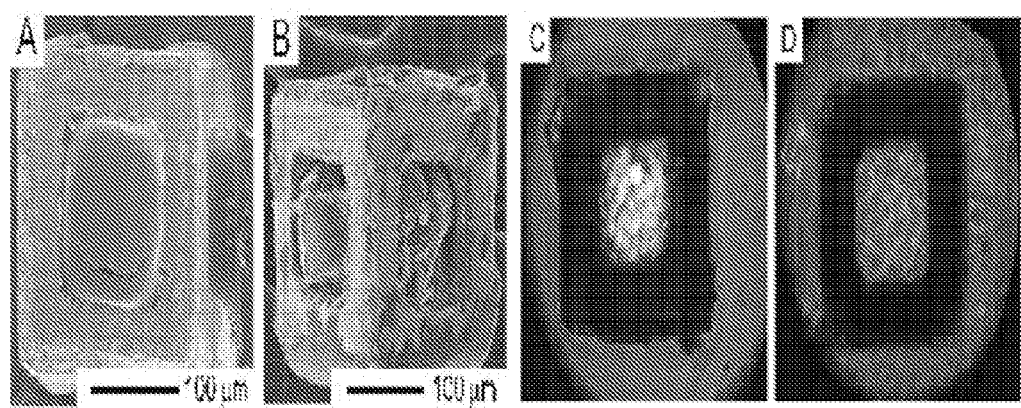
FIG. 8: SEM and optical images of boxes filled with (A & B) Pluronic hydrogel and (C) MDA-MB-231 breast cancer cells embedded in extracellular matrix (ECM) gel. (D) The cells could be released from the box by pulsatile agitation in cell media.

Loading:

To demonstrate that the boxes could function as encapsulation devices, they were loaded with a variety of medically relevant constituents including gels, beads, liquids, and cells (FIG. 8). For easy visualization, boxes with all open faces were used. However, in real applications, boxes with only one open face for loading, with the other faces closed or porous, would be used.

The hydrogel Pluronic F127 (20% solution) exhibits a thermoreversible transition from a liquid solution, at low temperature (e.g. 4° C. to an ordered micellar cubic phase at room temperature. This property makes it very attractive in the storage and release in drug delivery. The hydrogel consisted of a 20% w/w mixture oaf Pluronic F127 (poly(ethylene oxide)-block-poly (propylene oxide) block-poly (ethylene oxide) copolymer, (BASF Corp. www.basf.com) in water. The sample was shaken using a vortexer to speed up the mixing process and stored at 4° C. before usage. In order to load the hydrogel in the box, a drop of the liquid solution was placed on the box. Due to the hydrophilic sidewalls of the metallic box, the solution readily entered the box. Boxes were also loaded with MDAMB-231 breast cancer cells embedded in extracellular matrix (ECM) gel (MDA-MB-231 cells are representative of rapidly proliferating or immortalized cells such as βTC3 cells used in diabetes therapy, and stem cells used in regeneration). FIG. 8C shows a box loaded with cancer cells that were briefly suspended in ECM gel at 4° C. The suspension was introduced into the box and was kept at 37° C. for 15 min to allow the ECM gel to polymerize. The cells were stable in the box, and could be released (FIG. 8D), by pulsatile agitation of the box. These experiments demonstrate that it is relatively straightforward to load the boxes with a variety of constituents.

Interaction with RF Fields:

Since the boxes are metallic they interact with RF fields and behave as Faraday cages. This feature has been used to detect and track the boxes remotely using magnetic resonance imagining (MRI). A characteristic signature was observed for both the Cu and the Ni boxes—there was a pronounced darkness in the region of each box. This hypointense signature facilitated ready trackability with MRI, at short echo times, without the need for a contrast agent, and highlighted a major advantage of these encapsulation devices as compared to existing polymeric systems.

Since the boxes interact with REF fields, this feature suggests the possibility of inductively heating the box using a remote RF field generated by passing an alternating current through a coil [E. J. W. Ter Maten and J. B. M. Melissen, vol. 28 no. 2, pp. 1287-1290, 1992; C. K. Chou, in 5th IEEE Conf. Instrumentation and Measurement Tech., 1998, pp. 69-77; J. S. Curran and A. M Featherstone, Power Eng. J., vol. 2, no. 3, pp. 157-160, 1988: K. Hamad-Schifferli, J. J. Schwartz A. T. Santos, S. Zhang and J. M. Jacobson, Nature, vol. 415, pp. 152-155, 2002]. Boxes composed of diamagnetic (Cu, Au) and ferromagnetic (Ni) metals were fabricated. When a box is placed in a coil through which an AC current is passed, an electromagnetic force is induced. According to Faraday and Lenz's Law, $E=-N\,d\phi/dt$, (1), where E is electromotive force (EMF) induced in the box, $\phi$ is magnetic flux generated in the RF coil, and N is the number of the coil turns. The induced EMF causes a current to flow in the box which can cause heating. The heat generated can be calculated as $P=E^2/R$, (2), where P is the heating power generated by the currents, and R is the resistance of the sample.

The alternating current in the box is subject to the skin-depth phenomenon, i.e. the current density decreases with depth. Since the thickness of the surfaces of the boxes can be controlled with a range of thicknesses limited only by the photolithographic aspect ratio used to pattern the 2D precursor boxes may be fabricated with wall thickness comparable to the skin depth to minimize the electrical resistance. Additionally, if the box is ferromagnetic (e.g. Ni), the heating is increased due to magnetic hysteresis. As the primary purpose of induction heating is to maximize the heat energy generated in the box, the aperture of the inductive heating coil is designed to be as small as possible and the box needs to be fabricated with a material that features low resistance and high permeability.

Figure 9:
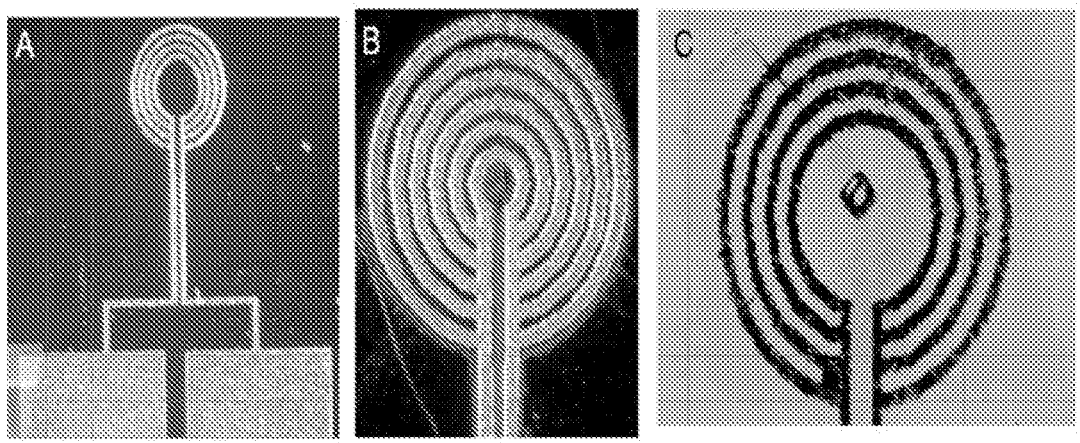
FIG. 9: (A&B) Optical images of 2D coils fabricated using photolithography. By passing current through the coils it is possible to generate a magnetic field. (C) The microbox is placed along the central axis of the coil in order to inductively heat the box.

Two kinds of configurations were demonstrated. In one case the boxes were introduced into a vial around which is wrapped a wire coil through which AC current is passed (200 MHz to 1 GHz, 0.1 to 1 Watt). In order to integrate heating, of the boxes with 2D microfluidics, and to maximize inductive coupling, 2D coils were also fabricated. The 2D coils are fabricated photolithographically (FIG. 9) and can be made with a variety of turns and spacing. The box is placed along the central axis of the coil in order to maximize inductive heating. Although the number of turns in the 2D coil is less than that of the 3D coil, the cavity of the 2D coil is comparable to the size of the box to maximize inductive coupling. Inductive heating characteristics of the boxes and the coils are being measured.

Figure 10:
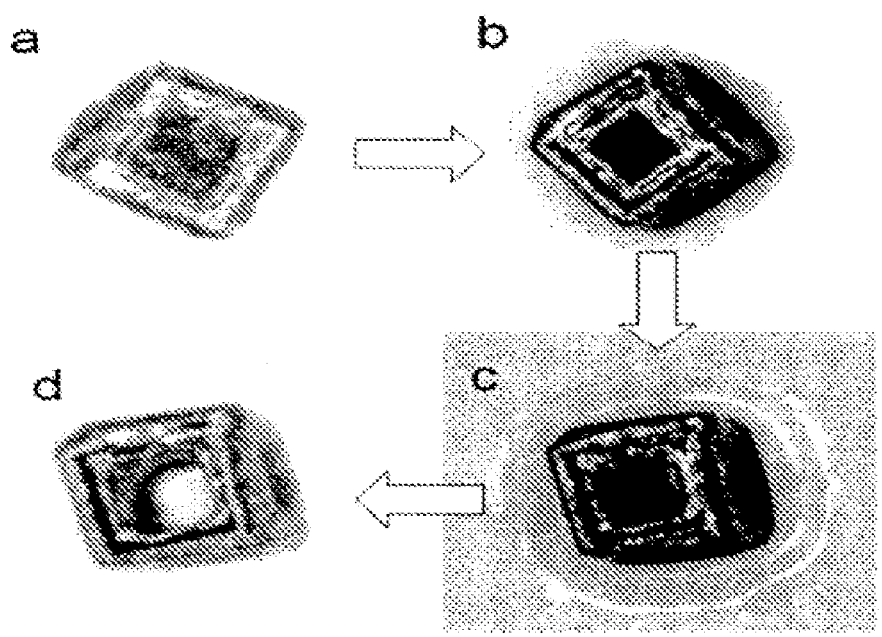
FIG. 10: Release of dye from a loaded box upon heating.

Releasing a Chemical from the Box Upon Heating:

In order to demonstrate that a chemical could be released from the box upon heating, the box was loaded with a hydrogel that was dyed red. Initially, one gram of Pluronic F88 (Molecular weight: 11400; melting point: 54° C.; obtained from BASF) was dissolved in 10 ml of acetone. The sample was then heated and sonicated to aid dissolution. A few drops of the dye erythrosine were added to the solution. An open faced box was loaded with the dyed hydrogel solution using a syringe and the box was allowed to sit until the acetone evaporated. Since the hydrogel dissolves in water, the loaded box was immersed in dodecane (hydrogel does not dissolve in dodecane) and placed on a glass slide. The slide was heated to 70° C. on a hot plate and optical photographs were taken at 3, 7 and 10 minutes. The gel softened and the dye was released into the dodecane solution. (FIG. 10). The release of chemicals from other hydrogels in water, as well as optimizing inductive RF heating of the loaded boxes, is currently being investigated. For in-vivo applications it will likely be necessary to heat the box approximately 10° C. above the temperature of the human body.

Conclusions

In summary, a new encapsulation device platform that combines the favorable aspects of three dimensionality with Si microfabrication has been demonstrated. Development of devices with nanoporous faces for cell encapsulation therapy (without immunosuppression) and designing boxes with optimized RF heating profiles for remote release of chemicals is in progress.

Example 4

Remote Radio-Frequency Controlled Nanoliter Chemistry and Chemical Delivery on Substrates Containers have been fabricated out of metal, which allowed them to be remotely coupled to electromagnetic sources. This feature was used to enable wireless control over both the spatial guidance (using magnetic containers) as well as the delivery of nanoliter volumes of chemical reagents. The containers can be guided in spatial patterns that are not limited by flow profiles in conventional microfluidics, that is, downstream from a channel inlet. The remote-controlled nanoliter containers enhance the capabilities of present-day microfluidics by enabling spatially controlled chemical reactions microfabrication within capillaries, and on demand localized delivery of chemicals to cultured cells.

A combination of conventional microfabrication and self-assembly [T. G. Leong, Z. Gu, T. Koh, D. H. Gracias, J. Am. Chem. Soc. 2006, 128, 11336-11337; B. Gimi, T. Leong, Z.

Figure 11:
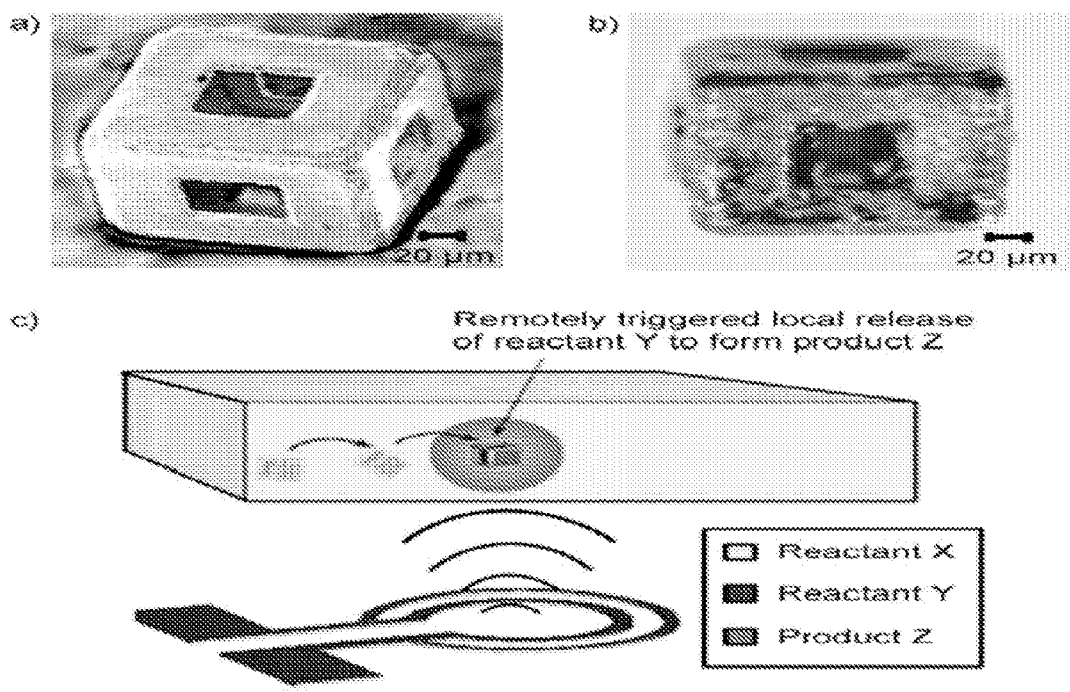
FIG. 11: a) A scanning electron microscope image of an empty container. The containers were three-dimensional (3D) porous cubes with a length of approximately 200 mm and a volume of 8 nL. b) An optical microscope image of a container loaded with a dye-soaked pluronic gel. c) A schematic diagram of the experimental set-up used to facilitate wireless microscale chemical engineering (not drawn to scale). Containers were manipulated using a magnetic stylus (not shown) and the contents of specific containers were released by directing an RF source towards the container. In the schematic representation, chemical Y is released from a specific container, chemical Y then reacts with chemical X in the surrounding medium to form product Z.

Gu, M. Yang, D. Artemov, Z. M. Bhujwalla, D. H. Gracias, Biomed. Microdevices 2005, 7, 341-345] were used to fabricate gold-coated, nickel nanoliter containers (FIG. 11a). To facilitate chemical delivery, the containers were filled with a gel that was soaked in the chemical reagent to be released (FIG. 11b). Two gels were used: pluronic 151 for general dry-release experiments and poly(N-isopropylacrylamide) (PNIPAm) [T. Hirokawa, T. Tanaka, J. Chem. Phys. 1984, 81, 6379-6380; M. E Islam, A. M. Alsayed, Z. Dogic, J. Zhang, T. C. Lubensky, A. G. Yodh, Phys. Rev. Lett. 2004, 92, 088303] for chemical delivery in aqueous solutions and to living cells. Pluronic is a water-soluble block copolymer hydrogel that softens at 52° C. and is compatible with a wide range of chemicals [P. Alexandridis, T. A. Hatton, Colloid Surf. Physicochem. Eng. Aspect. 1995, 96, 1-46]. Hydrogels based on PNIPAm 16 are thermoresponsive materials that are widely used in drug delivery, because they undergo a structural transition near the temperature range of the human body [H. Yu, D. W. Grainger, J. Controlled Release 1995, 34, 117-127; K. S. Soppimath, T. M. Aminabhavi, A. M. Dave, S. G. Kumbar, W. E. Rudzinski, Drug Dev. Ind. Pharm. 2002, 28, 957-974]. This transition temperature, as well as the collapse kinetics of PNIPAm, can be altered by adding co-monomers and changing the degree of cross-linking [R. A. Stile, W. R. Burghardt, K. E Healy Macromolecules 1999, 32, 7370-7379]. Hence, PNIPAm is an ideal candidate for remote-controlled release to living cells and in liquid media.

Once loaded, a container was placed in the reaction vessel of choice and could be guided in any spatial trajectory using a magnetic stylus. After guidance to the desired location, a radio-frequency (RF) field, generated by a 2D microcoil, was directed towards the container. The power in the RF field coupled inductively to the metallic container, thereby producing eddy currents in the frame and heating it up by a Joule effect. It is possible to heat even nonmagnetic metallic containers by inductive coupling, and the heating mechanism is different from that used to heat polymeric magnetic microspheres. Since the containers were microfabricated, the electrical characteristics could be made reproducible, and the temperature could be precisely controlled by changing the incident power. This reproducibility should be contrasted with the power needed for release from polymeric magnetic microspheres, which can vary greatly because of polydispersivity in sizes and inhomogeneous distribution of magnetic particles Within different microspheres.

By heating the container, the gel encapsulated within it softened (or collapsed) and released the chemical at the targeted spatial location (FIG. 11c). The metallic containers are essential to obtain heating at the power and frequency settings used. No release was observed from the gel in control experiments (on exposure to the RF radiation, but in the absence of the container) because of negligible dielectric heating at the frequency and power settings used (see the Supporting Information).

Figure 12:
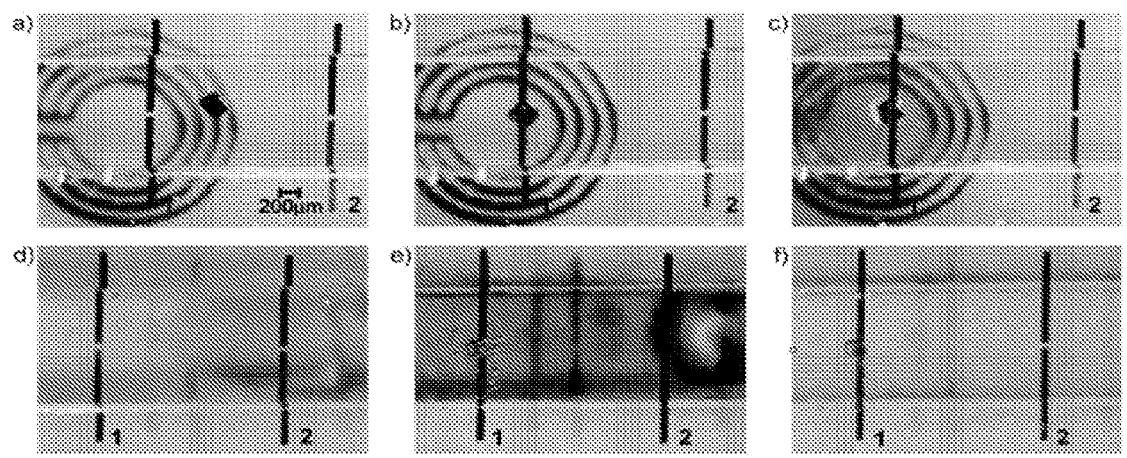
FIG. 12: Optical images showing the remote controlled, spatially localized microfabrication within a capillary. Two microwires (1 and 2) were embedded within a microfabricated capillary (ca. 1 mm in diameter and 1.5 cm in length) and the capillary was aligned on top of a 2D microcoil, a, b) First, a container filled with pluronic and soaked with the chemical sensitizer was guided into the capillary to the site of the gap within wire 1 using a magnetic stylus. c) The chemical sensitizer was released by remotely heating the sensitizer-soaked pluronic gel that was encapsulated within the container. This heating was achieved with the 2D RF coil. After sensitizing the gap, the first container was removed, a second container was guided to the same gap in microwire 1, and the activator was released by heating the pluronic gel remotely. d) After activation, the second container was also removed. e) The capillary was then flushed with a commercial electroless copper-plating solution; chemical reduction (bubbles of the hydrogen gas, a byproduct in the reaction, can be seen) of copper sulfate to metallic copper, occurred at the gap within microwire 1. f) Copper was deposited only in the gap between microwire 1, no copper was deposited in the gap in microwire 2.

The remote-controlled containers make it possible to do chemistry with unprecedented spatial control in hard-to-reach regions. To highlight this feature, we repaired a break gap in one of two adjacent microwires embedded within a capillary; the capillary was accessible only by input and output ports (FIG. 12). The gap within microwire 1 was repaired by remotely guiding containers to that site in air (FIG. 12a,b) and remotely releasing first a chemical sensitizer and then an activator (using two separate containers) locally at the site of the gap (FIG. 12c). The sensitizer and activator were tin and palladium catalysts, respectively, which facilitated the electroless deposition of copper. After sensitizing and activating the spatial region within the gap of microwire 1 only (FIG. 2d), the entire capillary was flushed with a commercial solution of copper sulfate (FIG. 2e). Although both microwires and the walls of the capillary were exposed to the copper sulfate solution, metallic copper deposited only at the chemically sensitized and activated gap in microwire 1 (FIG. 12f). Electrical resistivity measurements confirmed electrical continuity of microwire 1 across the gap. This result demonstrates the utility of the containers for localized chemical delivery and chemistry within capillaries and other small spaces. In comparison to already existing methods of microfabrication in capillaries, [J. C. McDonald, G. M. Whitesides, Acc. Chem. Res. 2002, 35, 491-499; M. Madou, Fundamentals of Microfabrication, CRC, New York, 1997; P. J. A. Kenis, R. Ismagilov, G. M. Whitesides, Science 1999, 285, 83-85] this invention's method is not limited by the geometry of the capillary or laminar flow profiles.

A second demonstration highlights the utility of the nanoliter containers in the remote-controlled, localized delivery of sub-nanoliter volumes of chemicals to specific cells cultured on substrates. Containers were loaded with PNIPAm soaked in a live/dead (green/red) two-color fluorescence viability stain [invitrogen live/dead stain product guide http://probes.invitrogen.com/] to stain cells locally in a culture dish and to verify that no necrotic cell death occurred during chemical release as a consequence of the heating [S. Corvin, S. Boexch, C. Maneschg, C. Radmayr, G. Bartsch, H. Klocker, Eur. UroL 2000, 37, 499-504] or exposure to the RF radiation.

Figure 13:
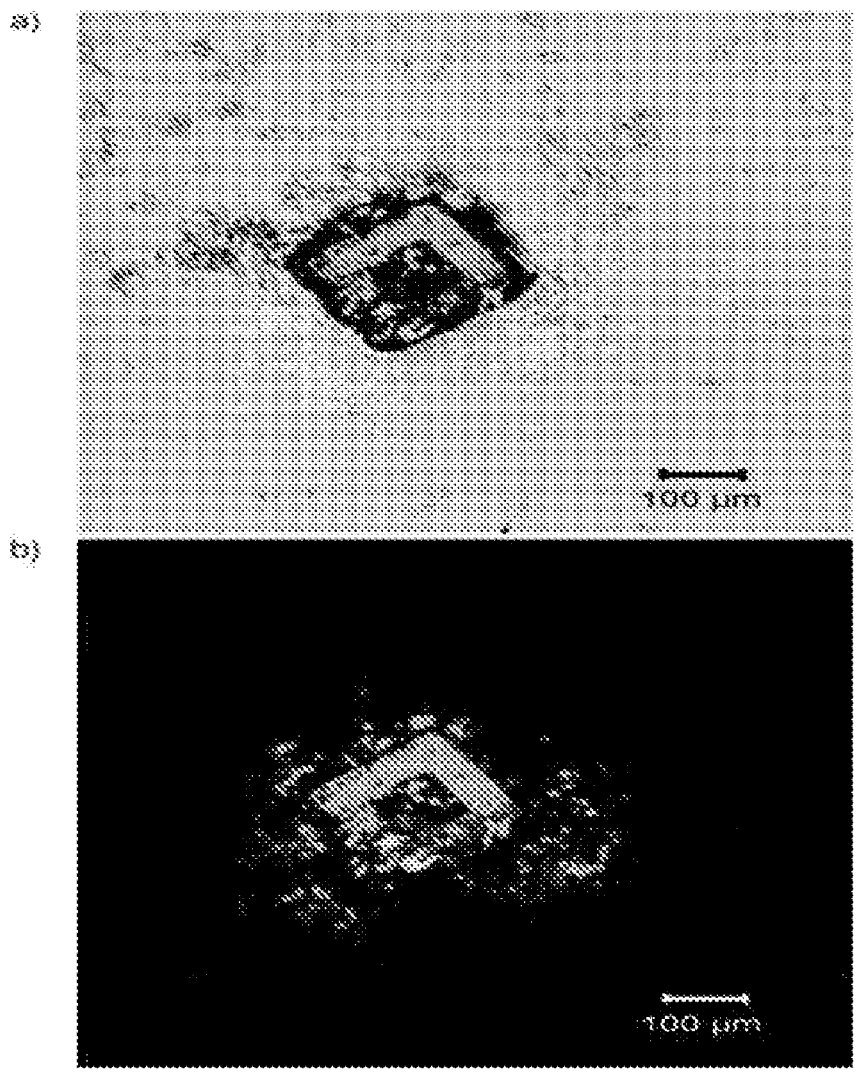
FIG. 13: Cell-viability assessment by live/dead fluorescent imaging of calcein AM and ethidium homodimer-1, both released remotely from the containers. a, b) Confocal images of the local release of the live/dead stain to L929 mouse fibroblast cells. No red cells were observed, thus indicating no necrotic cell death during the release. a) Transmitted light differential interference contrast (DIC) images showing both the cells and the container. b) Fluorescent image showing only localized cell staining.

The L929 mouse fibroblast cells were cultured in 35-mm well-plates with glass inlays and grown to confluency. At the start of the remote-release experiment, the growth media was removed and the cells were rinsed with phosphate-buffered saline to dilute the serum esterase activity, thereby minimizing background fluorescence. To enable remote release of the stain, an RF coil was placed below the plate directly under a container, and the coil was powered up at 2-3 W for 1 minute to collapse the encapsulated PNIPAm and release the stain. Fluorescent images were obtained 30-60 minutes after release, to allow sufficient time for uptake of the stain. It is clear from the confocal fluorescence images (FIG. 13) that the stain was released locally and within a radius of less than 500 ltrn from the center of the container. It can also be seen that the cells exposed to the stain had green fluorescence, thus indicating that they were alive, and no red fluorescing, or dead cells were observed. The results indicate that neither the temperature used to collapse the encapsulated PNIPAm nor the RF radiation caused necrotic cell death. It should be noted that no leakage or spontaneous release (that is, no cell staining) was observed from the containers in experiments where no RF field was applied. Biocompatibility studies show no necrotic cell death occurs in the presence of the containers over 48 h.

In conclusion, the metallic, self-assembled nanoliter containers can be utilized for remote-controlled microfabrication and chemical delivery in hard to reach spaces. The containers will be useful in fabricating complex and reconfigurable microanalytical, microfluidic, and micro-electromechanical systems. The localized remote delivery of chemicals to cells establishes a methodology for remotely manipulating the chemical and biological micro-environment for applications in cell engineering, tissue engineering, and drug development. Finally the containers provide an attractive platform for the integration of additional features of wireless devices (for example, frequency-selective remote control and remote communication) with the delivery of nanoliter volumes of chemicals.

Experimental Details
Fabrication of the Microcontainers:

Briefly, the fabrication process involved the self-assembly of a two dimensional (2D) template into the 3D cubic container. First, 2D metallic templates consisting of six square porous faces were photolithographically patterned. A second layer of photolithography was used to pattern solder hinges on the outer edges and in between faces. The 2D template spontaneously folded into the 2D cubic container when it was heated (in a fluid) above the melting point of the solder hinges, wherein the surface tension of the molten solder provided the force to drive self-assembly. The final size and porosity of the 3D container was varied by patterning the 2D template appropriately. In this experiment, containers were fabricated from nickel (Ni) a magnetic material, to enable remote guidance. The outer and inner surfaces of the containers were coated with gold (Au) to increase biocompatibility and decrease electrical resistance (low electrical resistance increases the skin depth for penetration of electromagnetic waves). The fabrication process was highly parallel and large numbers of containers could be fabricated in a cost-effective manner.

Preparation of the Gels:

Pluronic®: The gel was made by combining 0.5 g of F68 Pluronic®(BASF) with 0.5 mL of water. The mixture was sonicated for 10 minutes to ensure complete mixing. Gelation occurred after excess water evaporated.

PNIPAm: The PNIPAm gel was made from two stock solutions A and B. Solution A consisted of 1.6701 g N-isopropylacrylamide (PNIPAm), 0.0083 g N, N'-methylenebisacrylamide (BIS), and 15 mL water. Solution B consisted of 0.0129 g of ammonium persulfate (APS) and 15 mL of water. Both solutions were vortexed until the solute dissolved. Gelation was achieved by mixing equal volumes of each solution together with 0.4% (v/v) of N, N, N', N'-tetramethylenethylenediamine (TMED) and occurred within 5 minutes.

Remote Guidance:

Remote guidance was achieved by manipulating a magnetic stylus below the reaction vessel. In order to reduce the friction between the containers and the surface of the vessel the stylus was rotated along the base of the vessel causing the containers to tumble along the surface.

The 2D RF Microcoil Set-Up

A 2D microcoil was fabricated using photolithography on a printed circuit board (PCB) as the RF source. The microcoil was placed either below or above the containers at separation distances of approximately 1-5 mm. A current at 800 MHz (RF) was passed through the coil to generate an alternating magnetic field in a direction perpendicular to the surface of the coil, an incident power in the range of 1-7 Watts was used. The surface of the coil was air cooled to remove any Joule heat generated in the coil.

Remote Repair of a Microwire within a Capillary:

Microwires (100 µm thick copper wires, spaced 2 mm apart) with break gaps of 50 µm were fabricated on a glass slide using photolithography. The capillary was formed using polydimethyl siloxane (PDMS) walls that were scaled against the glass slide (containing the wires) and another glass slide (the roof of the capillary). Sealing was achieved by plasma surface modification of the PDMS). The capillary with the embedded wires (FIG. 12A), was approximately 1 mm in width and 1.5 cm in length and was only accessible by the input and output ports at its two ends.

The sensitizer soaked Pluronic® gel was prepared by combining 0.5 mL of sensitizing solution (Transene) with 0.5 g of Pluronic F68 (BASF). The activator soaked Pluronic® gel was prepared by mixing 0.5 mL of activating solution (Transene) with 0.5 g of pluronic F68. Prior to loading, each mixture was sonicated for 5 minutes to ensure complete mixing. A 1 µL drop of each of the mixtures was placed on two separate containers and the solutions were allowed to gel overnight (~14 hours). The containers were then cut out of the gel, to ensure that the gel remained only within the container.

After guiding the containers to the gap within microwire 1, we first applied 4 Watts of power to the 2D coil until the gel softened and released the sensitizer solution from the container. Then the power was reduced to 3.0 Watts for 1 minute to allow sufficient time for diffusion of the solution through the gel and to the surface of the gap. The channel was then flushed with water to remove the container and excess gel. This process was then repeated for the second container filled with the activator solution.

An electroless copper solution was made by mixing commercial solutions, PC electroless copper solution A and PC electroless copper solution B (both from Transene), in equal volumes. A syringe with a diameter of 0.9 mm was fitted with 0.8 mm ID tubing. The other end of the tube was placed in one opening of the channel. A syringe pump (RAZEL) was used to flow the plating solution into the channel and over the broken microwires. A pulsatile flow was used to facilitate the plating reaction by maintaining a high local concentration of copper ions while allowing sufficient time for deposition. During the experiment, the copper plating solution was kept at 45° C.

Remote Controlled Delivery to Living Cells:

Containers were loaded with PNIPAm and allowed to sit overnight. On the day of the experiment, the Live/Dead® two-color fluorescence stain (Invitrogen) was prepared at concentrations of 0.5 µM Calcein AM and 1.0 µM Ethidium homodimer-1. The PNIPAm filled containers were submerged in the stain solution for 3.5 hours prior to beginning the experiment to allow the PNIPAm ample time to rehydrate and absorb the live/dead stain.

L929 mouse fibroblast cells (Sigma) were cultured and maintained following standard cell culture protocols. The cells were cultured in 75 cm2 culture flask in 85% Minimum Essential Medium Eagles containing L-glutamine and sodium bicarbonate with 10% horse serum and supplemented with MEM non-essential amino acids and sodium pyruvate. The cells were maintained in an incubator set to 37° C. with a water-saturated 5% CO2 atmosphere. L929 cells were sub-cultured 2-3 times per week utilizing trypsin-EDTA and seeding the new flask at a density of $3 \times 10^4$ cells/mL. The seeding density was verified by removing a sample of the trypsinized cells, staining the cells with trypan blue and using a hemacytometer to count the number of viable cells.

Remote release experiments were conducted in 35 mm well-plates with glass inlays (Glass-bottom-dishes inc.) for optimum confocal microscopy. Briefly, cells were seeded at a density of 250 tL of $2 \times 10^5$ cells/mL directly onto the glass inlay and allowed to rest for 30 min to promote adhesion. Two mL of growth media was then added and the cells were incubated for 48 hours to achieve a confluent monolayer.

After remote release, the cells were imaged using a Carl Zeiss confocal microscope. Briefly, the microscope was setup with lasers and filters recommended in the Live/Dead® assay protocol. Calcein AM was excited at 488 nm and ethidium homodimer-1 was excited at 543 nm. Dye uptake was detected with filter cubes of BP 505-530 (for calcein in live cells) and LP 650 (for ethidium homodimer in dead cells).

Figure 14:
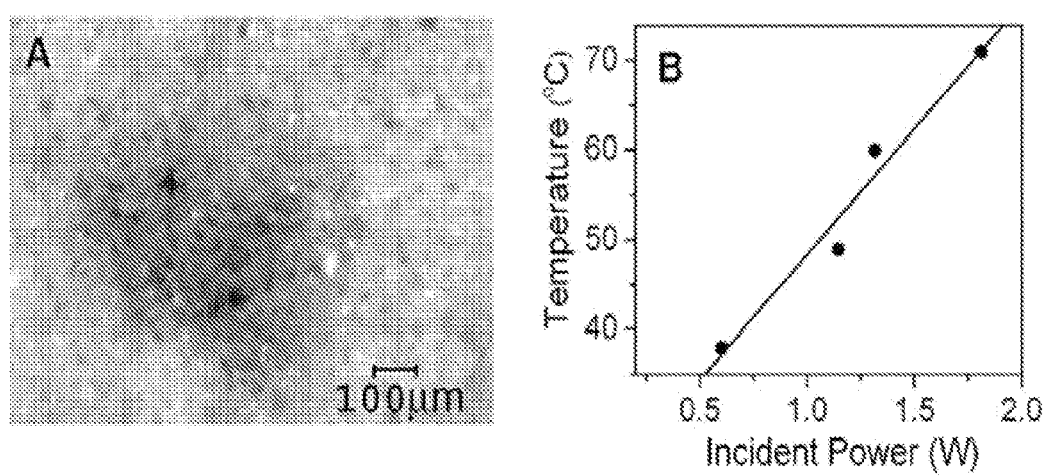
FIG. 14: (A) Optical image of the color change observed on a temperature indicator label placed under a nanoliter container, exposed to RF radiation. The color change occurs only under the container showing that the heating is local. (B) A plot of the temperature, measured using the color indicator label vs. the incident RF power.

Control Experiments
Heating Characteristics:

To demonstrate control over heating of the nanoliter containers with the incident power of the magnetic field generator, a temperature control experiment was conducted. The setup of the experiment was similar to our other RF controlled release experiments. The only difference was the placement of a Non-Reversible OMEGALABEL Label (Omega TL-S series) under the nanoliter container so that it could be heated with good thermal contact. The temperature of the container surface can be deduced color changes in the labels that occur at 38° C., 49° C., 60° C. and 71° C. respectively. The incident power of the magnetic field was increased until the specific label changed color (after waiting for approximately 30 seconds). FIG. 14(a) shows the color change in the label over which the container was placed FIG. 14(b) is a plot of the temperature measured by the labels vs the incident power. Hence, by changing the incident power the heating could be precisely controlled. It should be noted that the exact depends on the specific container used and the experiment (i.e. dry or The color change occurs only under the container showing that the heating is wet release, surrounding local. (B) A plot of the temperature measured using the color indicator label environment) vs the incident RF power High Spatial and Material Selectivity of Remote Release from the Containers To demonstrate the material and spatial selectivities, the following control experiment was performed. Two containers loaded with Pluronic® gel (soaked with food coloring) were placed 3 mm apart from each other in a Petri dish. Another isolated piece of gel (not encapsulated within a container) was also placed in the dish. The Petri dish was aligned over a 2D microcoil at a distance of 2 mm, such that in the plane of the dish, the isolated piece of gel was aligned directly over the center of the coil; one of the containers was aligned within the circumference of the coil but offset from the center by 300 µm; and the second container was misaligned and lay outside the 2D coil. The coil was powered up at 800 MHz. Only the gel within the container aligned within the circumference of the coil heated up and softened at a power of 4.7 Watts. Even when the power was increased to 7 Watts, the isolated piece of gel placed in the region of highest field as well as the gel in the misaligned container remained unchanged. This control experiment demonstrates that the inductive heating had high spatial and material selectivity. The experiment also shows that the metal used to fabricate the nanoliter container is essential to enable the inductive heating. It should be noted that a magnetic material is not required to facilitate remote heating (the magnetic property is used merely for spatial guidance). Also demonstrated was the release from containers with no Ni, i.e., composed of copper/gold.

Figure 15:
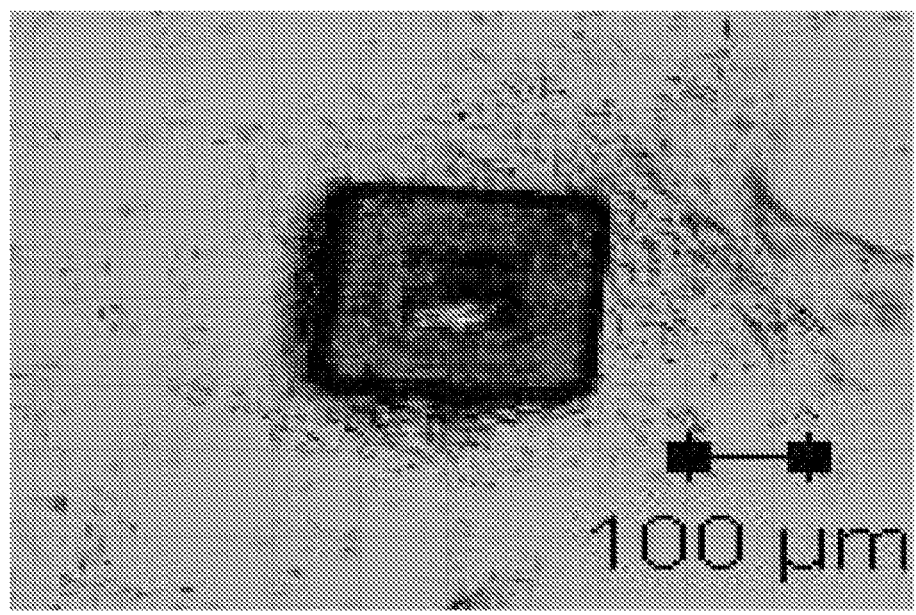
FIG. 15: (Confocal microscopy image of a nanoliter container loaded with PNIPAm gel soaked with LIVE/DEAD© assay. The experiment followed the test procedures with the exception that the RF was not turned on. The absence of cell staining, surrounding the container (compare with FIG. 13) demonstrates no discernable chemical release in the absence of the RF radiation trigger.

No Diffusion of Chemicals in the Absence of RF Radiation:

A control experiment was performed to demonstrate absence of diffusion of the LIVE/DEAD° assay (i.e. demonstrate no spontaneous leakage of chemicals) from loaded nanoliter containers, in the absence of RF radiation. The experiment followed the test procedures with the exception that the RF was not turned on. This helped to ensure that the tine frame for exposure was the same. Confocal microscopy was used to verify that no leakage of the Live/Dead assay had occurred from the PNIPAm in the absence of RF radiation (remote heating) over the time scale of the experiment (FIG. 15).

Example 5

Surface Tension Driven Self-Folding Polyhedra

Fabrication of Patterned Polyhedra:

The first step in the process involved the fabrication of 2D templates composed of patterned faces and solder hinges that would eventually fold up into 3D hollow polyhedra. A polymeric sacrificial layer made of polymethyl methacrylate was spin-coated onto a silicon (Si) substrate to facilitate subsequent release of the 2D templates. A metal seed layer was then evaporated onto the sacrificial layer to create wafer-scale electrical contact for subsequent electrodeposition steps. The faces were patterned using photolithography and fabricated using electrodeposition. Since conventional photolithography was used to pattern faces, any arbitrary pattern could be incorporated. Faces composed of either copper (Cu) or nickel (Ni) were fabricated; choice of metals was determined by cost, etch selectivity with respect to the seed layer, ease of deposition, and the need for magnetic functionality. A second layer of photolithography as used to pattern the solder hinge templates. After hinge patterning, the exposed seed layer in the hinge region bounded by the faces was etched to disconnect the underlying seed layer only between the faces, while retaining electrical continuity with the rest of the seed layer at the face corners. The solder hinges were electrodeposited, and then the 2D template was released from the substrate by etching the remaining seed layer and dissolving the sacrificial layer. A template composed of six square faces, arranged in a cruciform and held together by solder hinges was used to form a cube. Apart from the solder in between faces, there is no other tether. Self-folding was carried out in a high boiling point solvent, N-methylpyrolidone (NMP), which was heated above the melting point of the solder (~188° C.). A small amount of #5 RMA (rosin, mildly activated) flux was added to the solvent to clean and dissolve any oxide layers on the solder and thereby ensure good solder reflow.

Design Considerations:

the design, Ni was always used as the topmost surface layer of the face in contact with the hinges. Even for the Cu polyhedra, the top of the faces were coated with a thin layer of Ni prior to hinge deposition. Solder does not wet Ni surfaces well, so the solder stays in the region where it is electrodeposited and does not spread across the entire surface of the face during folding (which occurs when solder is in contact with Cu). When the Ni coating was absent, we still observed folding, however the yields were poor. The low yield was a result of the solder migrating away from the regions where it was deposited, thereby making it very difficult to control the volume of solder in the hinge region between faces (which ultimately determines the final folding angle).

The design of the 2D template ultimately determines the final shape and porosity of the polyhedra. Shown in FIG. 1A is a typical 2D layout of the faces and hinges. Autodesk® AutoCAD 2005 was used to generate the layout file used to fabricate two photomasks (one for the faces, one for the hinges). To fabricate a cube, square faces separated by a gap, g of 10-15% of the face dimension, L, in FIG. 1A, were typically used. Some tolerance in the gap width was observed, as the molten solder tends to draw the faces laterally towards each other during folding. It should also be noted that since the gap width is 10-15% of L, it was often the minimum feature size of the photomask and lithography process, e.g., for 15 µm cubes, the required gap width of 1.5-2 µm represented the smallest lithographically patterned feature.

In contrast with prior surface tension-based self-folding work, two types of hinges were used: internal ones between faces (folding hinges) and external ones at the periphery of faces (locking hinges). The folding hinge width (shown as W in FIG. 1B) was 25% of L, and the hinge length was 80-90% of L. If the folding hinge lengths were smaller (<80%), the cubes formed were not seated completely at the corners. Longer hinge lengths (>90%) were unnecessary, since neighboring hinges would overlap at the corners. Additionally, hinge lengths of 100% were incompatible with the fabrication process; these hinge patterns resulted in the complete removal of the seed layer at the perimeter of the 2D templates during the etch step after photolithography of the faces. This removal formed in an electrically discontinuous seed layer that prevented subsequent electrodeposition of the hinges. Reflow of the folding hinges provided the torque to rotate adjacent faces. Locking hinges that had the same length but half the width of the folding hinges played a secondary role in the folding of the 2D template; they functioned as a stabilizing stop, increased fault tolerance in folding, and ensured a final fold angle of 90° [Syms, R. R. A. *J. Microelectromech. Syst.* 1995, 4, 177-184]. Additionally, locking hinges increased the mechanical strength and sealed the edges of the polyhedra when two half-sized locking hinges fused and formed a single hinge containing, the equivalent volume of a folding hinge. Folding was complete within seconds when the locking hinges met and fused with each other. The fusion occurred as a result of the minimization of interfacial free energy between the molten locking solder hinge on each face and the surrounding liquid. On cooling, the solder hinges solidified and the polyhedral structure was locked in to place.

Finite Element Simulations:

In order to better understand the self-assembly process, we performed finite element simulations using the software program Surface Evolver [Surface Evolver was developed by Ken Brakke from the Susquehanna University Department of Mathematics. The latest Windows version v2.26c, updated Sep. 13, 2005 was used]. Surface Evolver determines the minimum energy surface for a given initial surface and a set of physical constraints, such as gravity, density, and surface tension. The iterations for evolving a minimum surface are controlled manually by the user. Scripts were developed to automate the task of varying parameters and evolving multiple surfaces. Simulations performed have included only two adjacent square faces held together by a single solder folding hinge since this captured the essential function of the folding hinges that play the critical role in forming, a well-folded structure. One face was assumed to be fixed, while the other was allowed to rotate freely around the solder hinge; this assumption parallels what was observed in experiments. To determine the equilibrium fold angle for a given geometry, we used the following strategy [Harsh, K and Lee, Y. C., *Proceedings of SPIE*; San Jose, USA, 1998]: minimal energy surfaces were generated for angles of rotation (out of the 2D plane) between 0° (flat) and 120° (overfolded) in incremental steps of 5°. The equilibrium angle corresponding to the global minimum energy was then determined from the minimum of the surface energy trend line versus angle plot, for a particular given face dimension.

Figure 16:
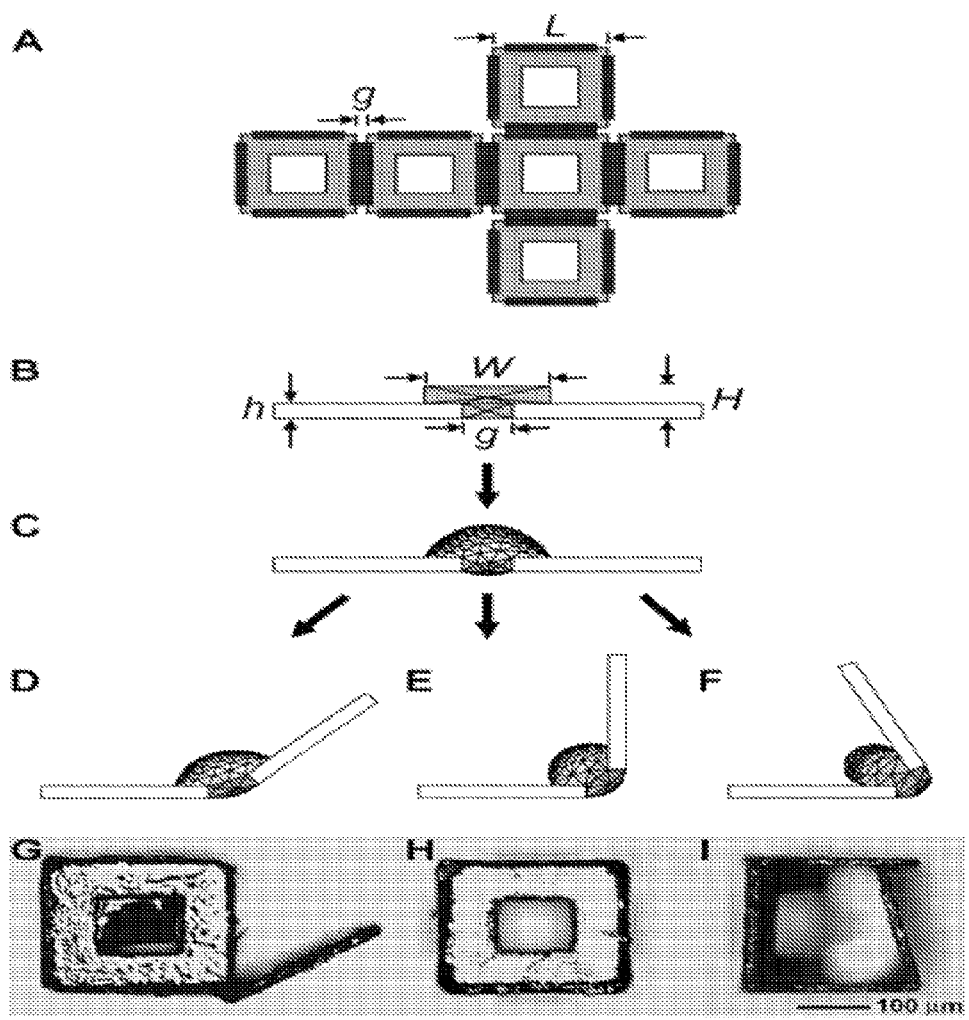
FIG. 16: Comparison of finite simulation and experimental results for the self-assembly process. (A) Top view (drawn to scale) with dimensions of the faces and gap widths of the 2D template used to self-assemble the cube. (B) Side view of two adjacent faces of the cruciform (as fabricated) with variables used in the finite element simulation. (C) Side view of adjacent faces at the onset of reflow of the folding hinge. (D-F) Finite element snapshots showing (D) underfolded, (E) right-angle folded, and (F) overfolded faces. (G-I) Optical microscope images of experimentally fabricated 200 μm cubes exhibiting the underfolded, right-angle folded, and over-folded faces. Note.
Figure 17:
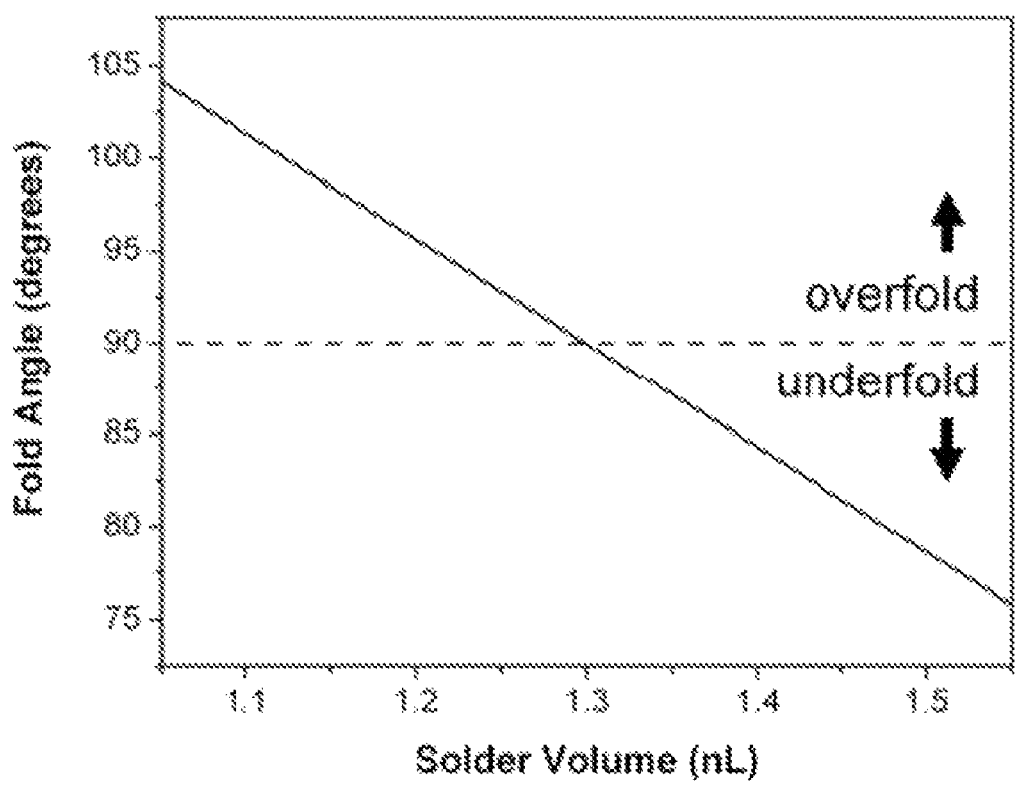
FIG. 17: Simulation results of the dependence of the fold angle on solder volume The results demonstrate that folding angle can be precisely engineered by controlling the solder volume at the hinge.

Shown in FIG. 16 (B-F) are illustrations of the finite element simulation for the folding process. In the 2D template, the folding hinge solder is in the form of a T-shaped right prism. On reflow, the solder liquefies and forms a rounded contour (FIG. 16C). Due to the high interfacial tension of the liquid solder (~481 mJ/m$^2$) [White, D. W. G. *Metall. Trans.* 1971, 2, 3067-3070], there is a strong driving force to minimize the exposed interfacial area between the molten solder and the surrounding fluidic liquid. This driving force causes the solder to ball up which results in the rotation of adjacent faces. The fold angle is primarily controlled by the solder volume. We observed evidence for this control in both simulations and experimental observations. Different solder volumes generated underfolded (FIG. 16 D, G), correctly folded (FIG. 16 E, H), or overfolded (FIG. 16 F, I) structures. A plot of the dependence of the fold angle on solder volume (generated by simulations, FIG. 17) shows that the fold angle decreases with increasing solder volume. Experimentally, the solder volume that determines the equilibrium fold angle was manipulated by controlling the height of the electrodeposited solder for a given hinge geometry.

Since the sealing properties of the process were of interest, the gravitational potential energy of both the solder and the faces were taken into account, in addition to the interfacial surface energy of the solder. It has been shown by others and verified in our simulations that the magnitude of gravitational effects are essentially negligible compared to the interfacial surface energy until sizes become large (i.e. mm scale). However, our inclusion of a gravitational energy term allowed us to determine the relative magnitudes of each of the forces as the feature sizes were scaled up or down. The fact that surface forces scale favorably with decreasing size is one attractive feature of surface tension driven self-assembly and has the potential to provide widespread utility in the assembly of microfabricated micro and nanoscale structures.

Figure 18:
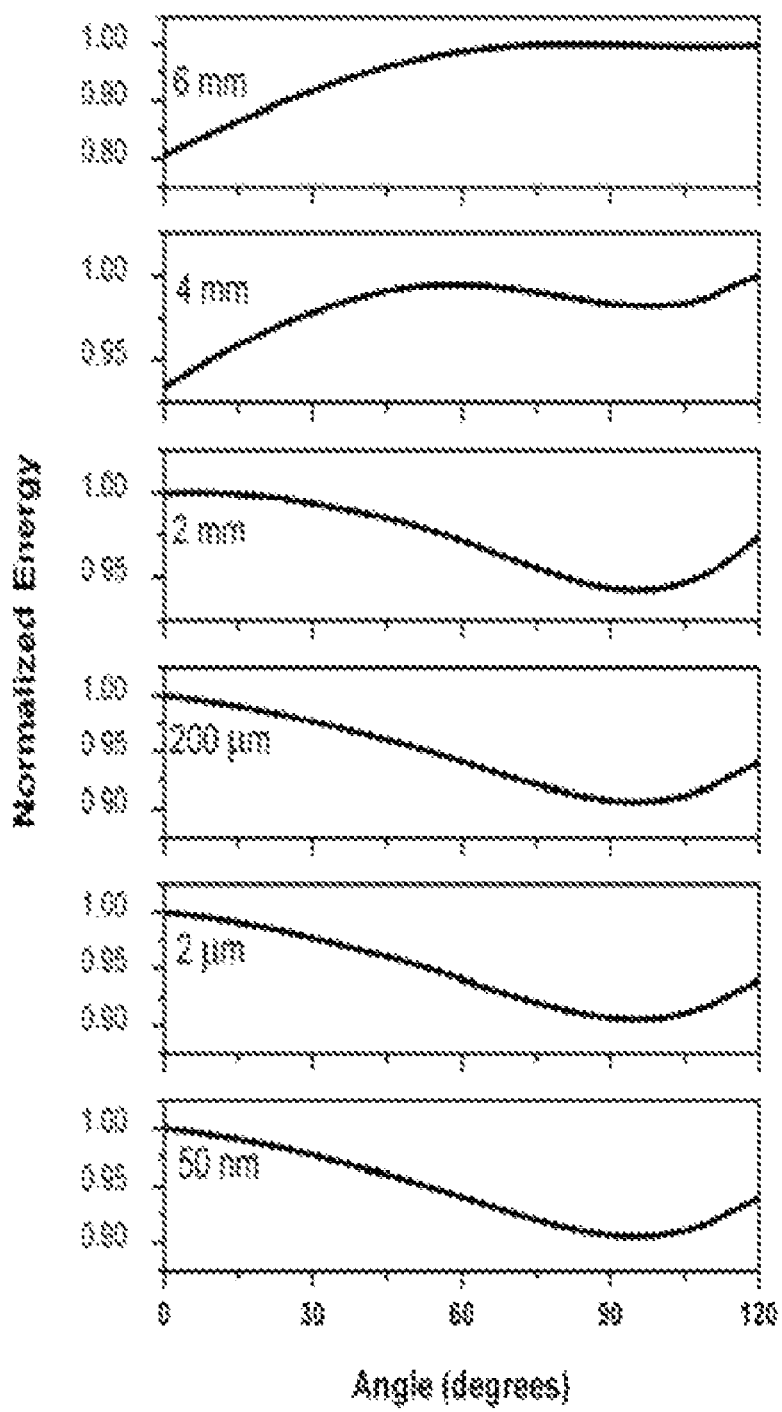
FIG. 18: Normalized total energy curves (finite element simulations) plotted as a function of fold angle for faces with lengths ranging from 6 mm to 50 nm. The curves show that folding is spontaneous at small size scales with stable minima. As the scale increases, gravitational forces increase and folding is no longer spontaneous (initial slope changes from negative to positive) and there is no minima present at 6 mm.

In order to determine the effect of size scaling on the folding process, simulations for 2D templates were performed with faces sized from the mm scale to the nm scale for a fixed solder volume. In each case, all dimensions (height, width, and length) were linearly scaled by the same constant factor. An energy landscape was observed (FIG. 18) which drives the folding process and that there are different energies for different fold angles (for a given geometry and solder volume). The initial slope of the energy curves indicates the magnitude of the rotational force of the faces and determines whether the folding process is spontaneous or not. A negative initial slope (FIG. 18, 50 nm to 2 mm curves) results in a spontaneous folding process while a positive initial slope (FIG. 18, 4 mm to 6 mm curves) indicates a non-spontaneous process. The minima in the curves (FIG. 18, 50 nm to 4 mm) around 100° are indicative of a stable, equilibrium folded configuration. The absence of a minimum in the curve for 6 mm faces implies the absence of any stable folded configuration, i.e. the two faces prefer to remain flat. These results can be explained by noting that as the size of the faces increases the weight increases and gravitational forces begin to dominate compared to the surface tension forces in the mm size scale. Hence, the initial slope of the energy landscape becomes positive in the mm range and the process becomes non-spontaneous. At smaller sizes, surface forces overcome gravitational forces and the process becomes spontaneous all the way down to the nanoscale. It should be noted that in the simulations, bulk properties for the materials and the solder were assumed and effects such as phase segregation, intermetallic formation, and diffusion within the solder were ignored; if these assumptions hold, it appears that the self-folding process would work on the nanoscale. For our standard geometry, material densities, and solder surface tension, our simulations show the maximum spontaneous folding size to be L≈1400 µm. Simulations also show that in an extreme case of a low surface energy hinge (10 dynes/cm, e.g. a liquid polymer) and heavy faces (20 g/cm$^3$, e.g. a dense metal folding is still spontaneous for polyhedra as large as 165 µm. This implies that it should be possible to fold structures with faces composed of almost any solid material and with hinges composed of virtually any liquefiable material up to a size scale of around 165 µm for our particular geometry.

Figure 19:
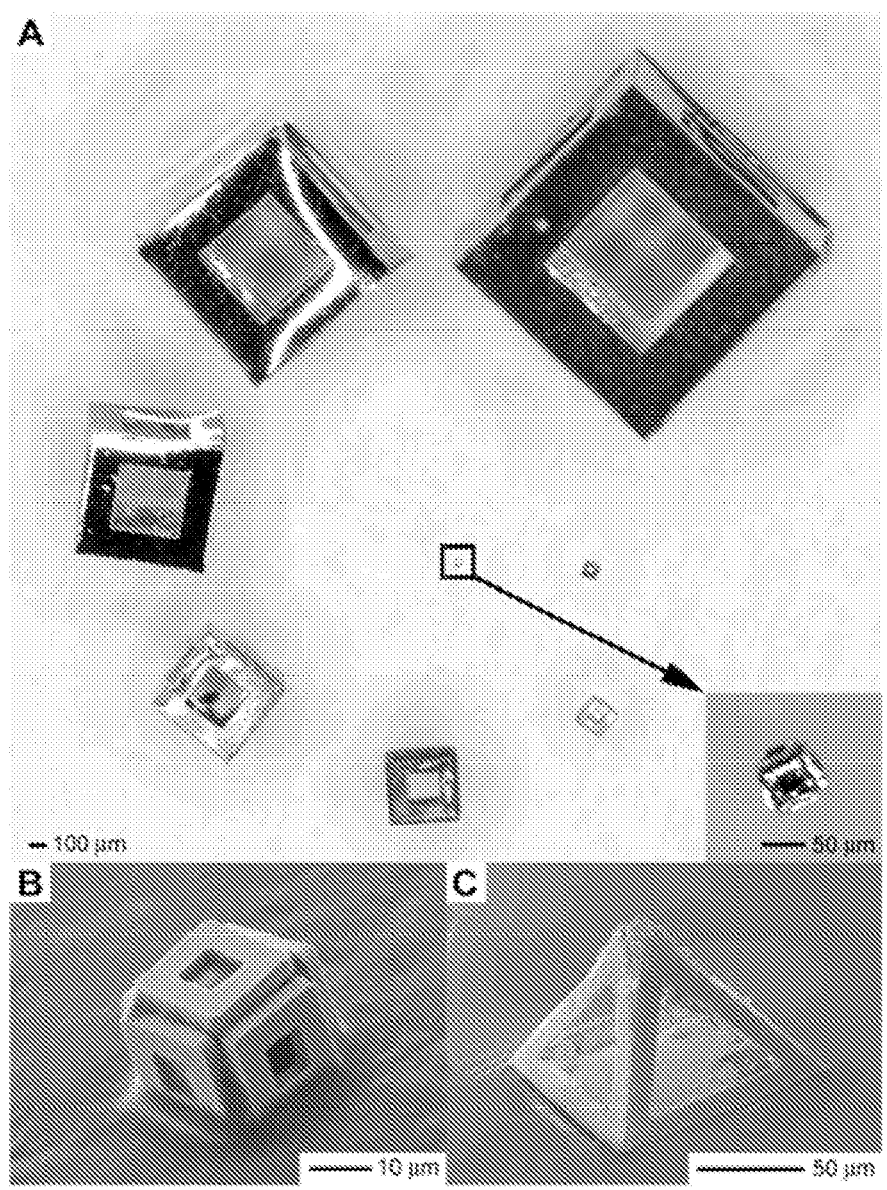
FIG. 19: (A) An optical image showing free standing polyhedra fabricated (experimental results) with a wide range of sizes all the way from (B) 15 μm and with different shapes e.g. (C) A square pyramid.

Experimental Results:

Experimentally, cubic polyhedra ranging in size from 15 µm up to 2 mm were folded (FIG. 19). We have also been able to fold polyhedra of other shapes (FIG. 19C). Although we believe smaller polyhedra can be fabricated we have been limited by our photolithographic capabilities. Below tens of microns, hinge gap widths approach the sub-micron size scale and alternative patterning techniques such as electron beam lithography, are required to fabricate the 2D templates. Our theoretical simulations show that folding of smaller polyhedra are spontaneous due to the large magnitude of the surface forces at small size scales. Although simulations show that the folding of polyhedra with large faces, i.e. 2 mm faces, is a non-spontaneous process, experimentally we were able to fold 2 mm cubes. We rationalize this result based on two observations. Firstly, agitation due to convection currents in the heated fluid occurs experimentally. This agitation can provide the initial driving force to lift faces marginally over the activation barrier for folding. Secondly, it should be noted that while we propositionally scaled all size variables in the simulations (e.g. a 2 mm face was simulated with a thickness of 80 µm) it was not possible to do so experimentally. Due to restrictions on the height of the photoresist and resolvable aspect ratios, we electrodeposited a thickness of only 12 µm for 2 mm cubes; the faces of the experimental templates thus had a substantially lower weight, increasing the threshold at which folding became non-spontaneous to larger sizes. Accounting for this fixed frame thickness in our simulation, we determined that the largest size for which the self-folding process would work for the materials used in our process is ~7 mm. Although we do not expect to use a lithographic process to fabricate structures as large 7 mm, the process of self-folding may still be relevant at this size scale, especially in the packaging of electronic devices.

Figure 20:
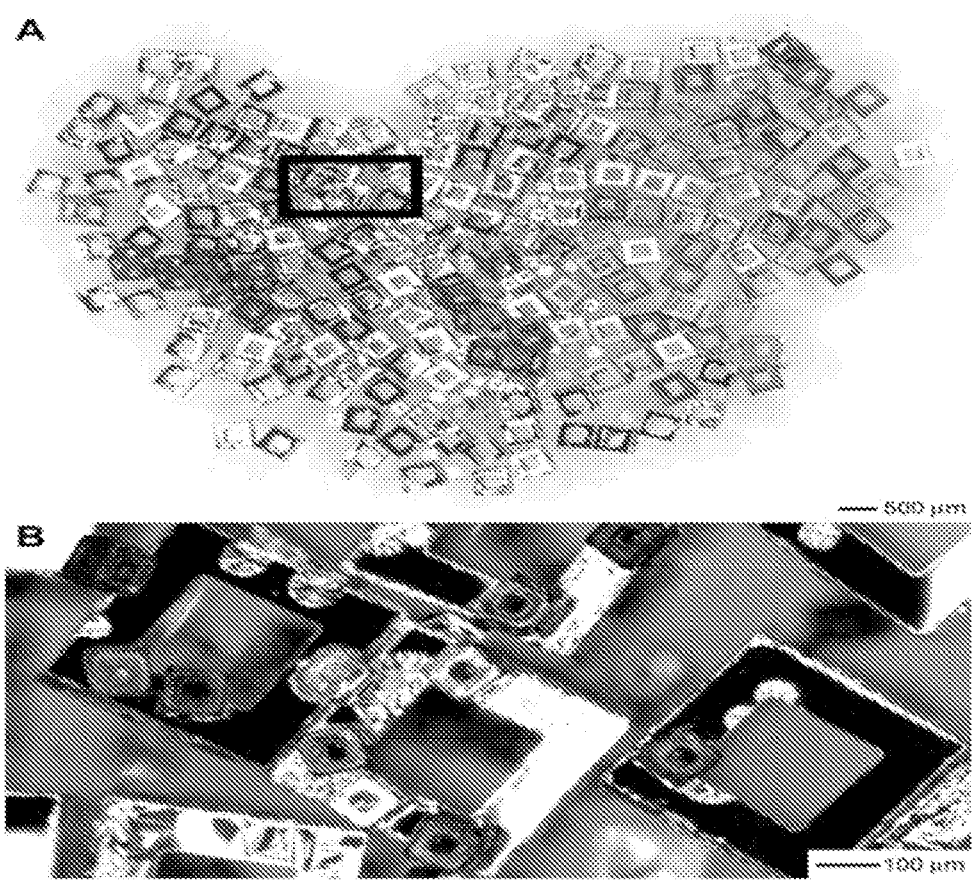
FIG. 20: (A) Optical image of cubes with a range of sizes formed in large numbers. (B) Zoomed in image of the outlined region in (A) featuring 100 μm cubes sitting on top of and among 500 μm cubes.
Figure 21:
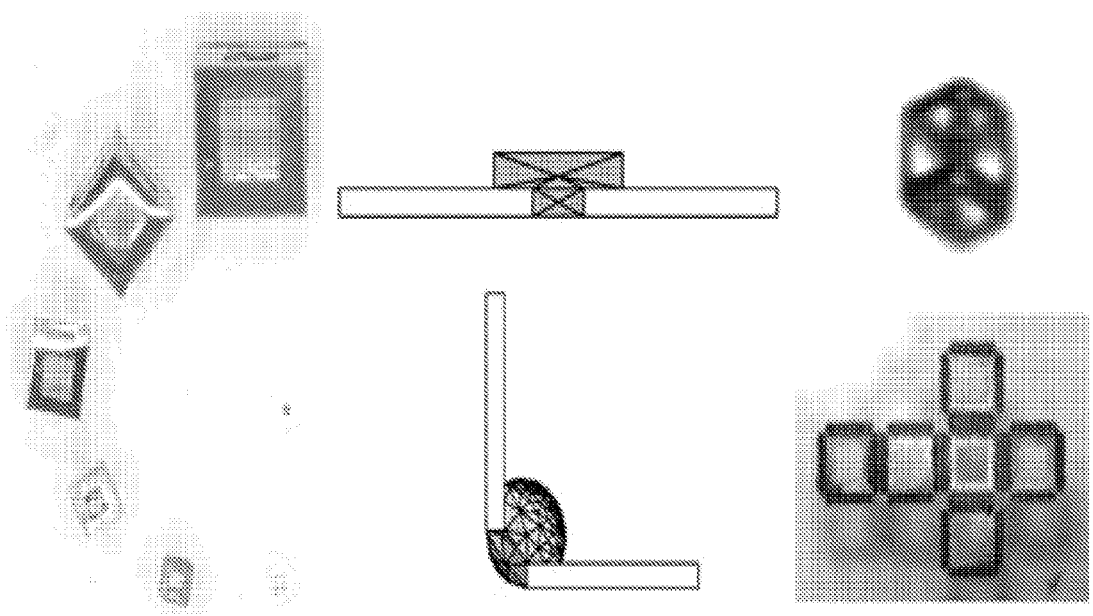
FIG. 21: Synopsis of folding process.

Tolerance of the Process:

Wafer scale patterning of the 2D templates is highly parallel, e.g. we pack approximately 1000 (L=100 µm) and 100,000 (L=15 µm) 2D cruciforms on a 3" wafer. The folding process is also highly parallel, and large numbers of 2D templates can be folded at once. Experimentally, the folding process also appears to be considerably fault tolerant and we have often been able to achieve yields in excess of 90% and fabricate large numbers of polyhedra (FIG. 20). We have also observed that folding occurred even when hinge registry was not perfectly centered across adjacent faces. Experimentally, to increase fault tolerance, we targeted our solder volume to result in a slight overfold (~100° of rotation from the horizontal). Since we used locking hinges, this overfold ensured that the faces met, allowing the locking hinges to fuse. This increased the tolerance of the process [Syms, RRA, *J. Microelectromech. Syst.* 1995, 4, 177-184] and sealed the cubes at the edges and corners. Additionally, convection currents existed in the hot solution during the folding process. These convection currents agitated the 2D templates and increased folding angle tolerance by encouraging the edges of the faces to collide; this allowed the locking solder hinges to fuse and hold the faces together with considerable strength [Jacobs, H. O. et al., *Science* 2002, 296. 323-325, Gracias, D. H. et al., *Science* 2000, 289, 1170-1172].

Conclusions:

In conclusion, a surface tension based folding process has been presented that can be utilized to fabricate untethered, hollow patterned polyhedra with a wide range of sizes from the mm to the nm. By leveraging well-established lithographic methods in microelectronics this fabrication process provides a route to incorporate precisely engineered monodisperse porosity, transistors, sensors, and other information processing devices on the polyhedra to create "smart particles." Using simulations, we have also demonstrated that the folding would work with a wide range of face materials and liquefiable hinges. This also demonstrates that the utilization of interfacial forces, which scale favorably at small sizes, is a useful paradigm for micro and nanofabrication.

Example 6

Spatially Controlled Chemistry using Remotely Guided Nanoliter Scale Containers

Along with conventional channel based microfluidic devices, several nanoliter scale chemical encapsulants have been developed, including those based on polymers, gels, and liquid drops [for example: (a) Lim, F.; Sun, A. M. Science, 1980, 210, 908-910. (b) Chang, T. M. S. Nat. Rev. Drug Discovery. 2005, 4, 221-235. (c) Langer, R. Acc. Chem. Res. 1993, 26, 537-42. (d) Tice, J. D.; Song, H.; Lyon, A. D.; Ismagilov, R. F. Langmuir 2003, 19, 9127-9133. (e) Hammer, D. A.; Discher D. E., Ann. Rev. Mater. Res. 2001, 31, 387-404. In contrast to the above organic systems, micromachined silicon-based devices can have extreme precision, high reproducibility, excellent mechanical strength, good chemical stability, as well as the ability to incorporate sensing signal conditioning, and actuating functions in close proximity or on the same substrate. However, 3D micromachined nanoliter scale reservoir systems with controlled porosity do not exist at the present time due to the inherent two dimensionality of the photolithographic process that is used in conventional silicon based micromachining.

Figure 22:
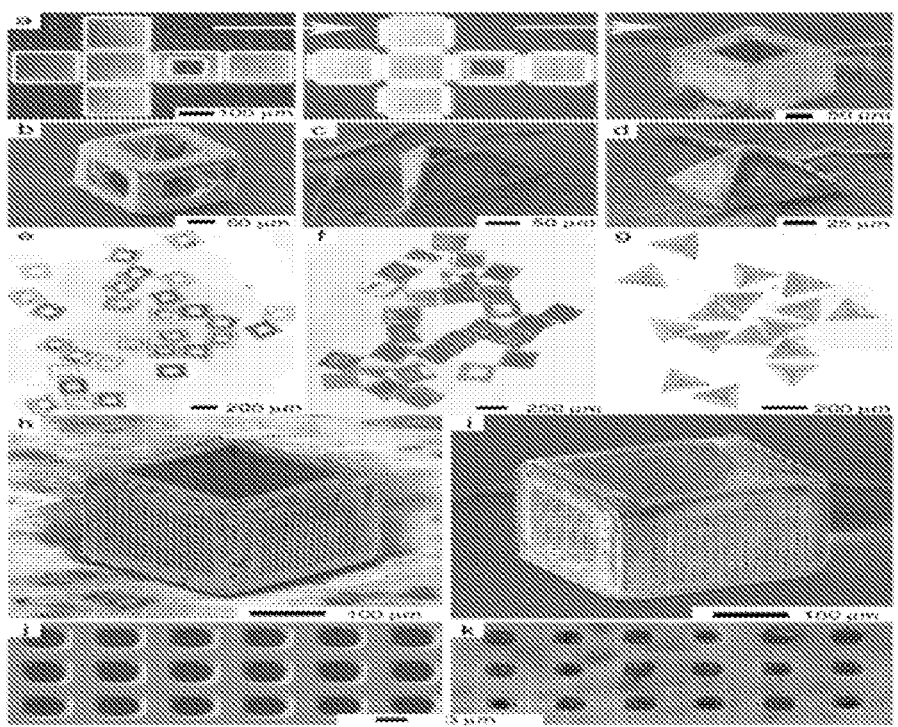
FIG. 22: (a) Optical and SEM images showing the different steps (the photolithographically fabricated 2D template, registry of solder hinges and the folded 3D structure) in the fabrication of a cubic container with one open face. SEM images of a (b) cubic container with all open faces, (c) pyramidal frustum, (d) square pyramid with an open face on the bottom. (e-g) Optical image of multiple containers of different shapes demonstrating the parallel fabrication strategy (h-k) SEM images of cubic containers with monodisperse pore sizes of (h, j) 5 microns and (i, k) 3 microns.
Figure 23:
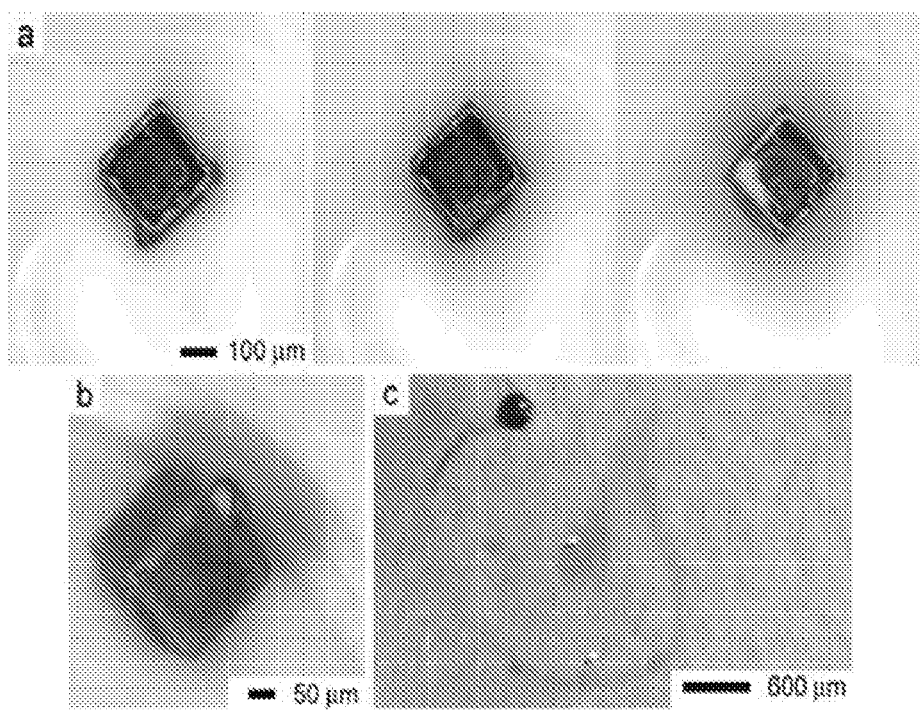
FIG. 23: Optical images of chemical release from containers (a) Spatially isotropic release of a dye from a container with identical porosity on all faces (b) Anisotropic release of a dye from a container with anisotropic porosity (five faces with an army of 5 micron pores, the sixth face has a 160 micron sized pore). (c) An example of a remotely guided spatially controlled chemical reaction. The letter G (for the Gracias Lab) was formed by the direct writing of phenolphthalein in an alkaline water-glycerol medium.

Demonstrated here is the development of 3D containers with precisely engineered surface porosity and their utility in chemical encapsulation, guided delivery, and spatially controlled chemistry. Briefly, the process involved the photolithographic fabrication of a 2D metallic template with solder hinges (FIG. 22a). The 2D template self-assembled into the 3D hollow polyhedron when it was heated above the melting point of the solder hinges, wherein the surface tension of the molten solder provided the force to drive self-assembly [(a) Syms, R. R. A.; Yeatman, E. M.; Bright, V. M.; Whitesides, G. M. J. MEMS 2003, 12, 387-417. (b) Hui, E. E.; Howe, R. T.; Rodgers, M. R.; IEEE 13th Int. Conf. MEMS, 2000 602-607. (c) Gimi, B; Leong, T.; Gu, Z.; Yang, M.; Artemov, D.; Bhujwalla, Z.; Gracias, D. H. Biomed. Microdevice 2005, 7, 341-3]. Containers have been fabricated with different shapes and volumes ranging from 230 picoliters to 8 nanoliters (FIG. 22a-d). The fabrication process was also highly parallel; containers of different shapes and sizes could be fabricated in a single process run (i.e. from a single wafer, FIG. 22e-g). When the process was optimized yields ranged from 60-90% (yields varied for different shaped containers depending on the number of folding faces and the symmetry) for a 3" wafer. The major yield limiters in the fabrication process were the photolithogaphic fidelity in the registry of hinges with respect to the faces, and the volume of solder in the hinges [Syms R. R. A. J. MEMS 1999, 8, 448-455. (15) Deng, T.; Whitesides, G. M.; Radhakrishnan, M.; Zabow, G.; Prentiss, M. Appl. Phys. Lett. 2001, 78, 1775-1777]. Since photolithographic microfabrication is highly precise, it was also possible to pattern one or more faces of the containers with monodisperse pores (FIG. 22h-k). The size of the pores formed was limited by the photomasks used (which in this case had a resolution of 3 microns). By controlling the porosity it was possible to engineer the reagent release profiles as shown in FIG. 23.

The containers were loaded using stereotactic microinjection with a solution of a gel (or polymer) and the chemical to be released. When the solvent evaporated, the gel remained within the containers. The chemicals were released by immersing the loaded containers in a solution that softened or dissolved the gel (or polymer). Since gels (and polymers) are available with a wide range of solubility and softening temperatures, it was possible to manipulate the chemical release rates using different solvents and temperatures. The images shown in the paper were obtained using containers loaded with a block copolymer hydrogel (Pluronic®). Release experiments were done in a water-alcohol based medium (Details in the Supplementary Section). By varying the relative porosity on different faces of the container it was possible to get both tisotropic (FIG. 23a) as well as anisotropic (FIG. 23b) chemical release profiles. Since the fabrication process was compatible with a variety of materials, it was possible to fabricate nickel based containers that could be remotely guided using magnetic fields. A spatially controlled (the letter G—any arbitrary trajectory is possible) chemical reaction was demonstrated by directly releasing (writing) a pH indicator phenolphthalein in a microwell filled with an alkaline solution (FIG. 23c). Direct writing was possible by manipulating the phenolphthalein-pluronic loaded container using a magnetic stylus that was moved under the microwell. It should be noted, that while guided manipulation was done using a permanent magnet, it is possible to use other well-developed microcoil based magnetic in manipulation circuits [Deng, T.; Whitesides, G. M.; Radhakrishnan, M.; Zabow, C.; Prentiss, M. Appl. Phys. Lett. 201, 78, 1775-1777] to reproducibly control the movement of the containers and hence the spatial release of the chemicals with arbitrary patterns.

Figure 24:
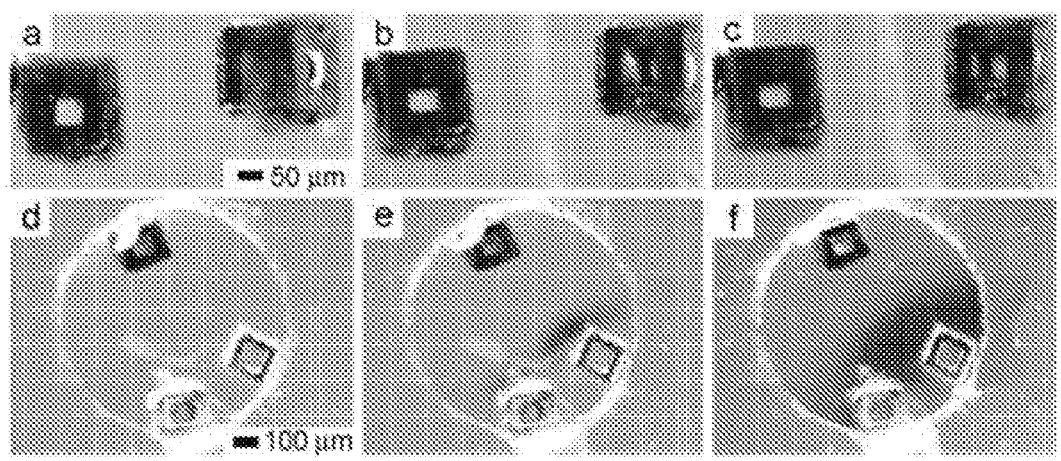
FIG. 24: Spatially controlled chemical reactions between multiple containers. (a-c) Reaction of copper sulfate and potassium hydroxide in an aqueous medium resulting in the formation of copper hydroxide along the central line between the containers. (d-f) The reaction of phenolphthalein (diffusing out of the two bottom containers) and potassium hydroxide (diffusing out of the top container) in an aqueous medium.

Spatially localized chemical reactions were also demonstrated between multiple nanoliter scale containers (FIG. 24a-c). When two containers loaded with copper sulfate and potassium hydroxide respectively were brought close to each other in an aqueous medium, a chemical reaction (to form copper hydroxide) occurred only along the central line between the two diffusing rates, the reaction occurred near the containers with the slower diffusing chemical (FIG. 24d-f). These experiments further demonstrate that the spatial control over chemical reactions can be extended to more complex reaction fronts involving multiple containers.

In conclusion, as opposed to all organic encapsulants, the containers allow unprecedented spatial control over the release of chemical reagents by virtue of their versatility in shapes and sizes, anisotropic faces, monodisperse porosity and their ability, to be guided in microfluidic channels using magnetic fields. Additionally, the metallic containers interact with remote electromagnetic fields that allow them) to be easily detected and tracked (using magnetic resonance imaging MRI). Thus, the containers provide an attractive plat-form for engineering remotely guided, spatially controlled chemical reactions in microfluidic systems.

Fabrication of the Microcontainers:

A 5.5 µm-thick sacrificial layer of poly(methylmethacrylate) (PMMA, MW: 996K) [Sigma-Aldrich, www.sigma-aldrich.com] was spun on a silicon wafer On top of the PMMA-coated water, a 15 nm adhesion-promoting chromium (Cr) layer and a 100 nm conductive seed copper (Cu) layer were evaporated. After the thin film deposition, we spin coated a layer of Shipley SPR220 7.0 photoresist [Rohm and Haas, www.rohmhaas.com]. The thickness of the photoresist was controlled via the spin speed and by varying the number of coatings applied. After a soft bake, the resist was exposed to UV light, using an Ultra µline Series Quintel mask aligner [Quintel Corp., www.quintelcorp.com] and patterned using a transparency mask. After developing the photoresist, electrodeposition was used to grow the metallic frames of the microcontainers within the photoresist mold to a height of 6-15 µm (depending on the characteristics required by various applications). We used commercial electrolytic solutions that contained the metal ions of choice [Technic, Inc., www.technic.com] to electrodeposit different metals. For the construction of non-magnetic containers, Cu was electroplated, and for magnetic containers, Ni was used. A second round of photolithography was performed in order to pattern the hinges. A layer of SPR220 was spun on top of the substrate and exposed to the hinge mask. Wider, internal hinges were located between adjacent faces, whereas the thinner external hinges resided at the outer edges of the frames. Alignment marks were used to ensure alignment of the hinges to the frames of the 2D precursors. After the hinge patterns were developed in 451 Developer, the exposed Cu (seed) and Cr (adhesion) regions in between the electrodeposited frames were etched using commercial etchants (APS-100 for Cu and CRE-473 for Cr [Technic, Inc., www.technic.com]). Tin/lead (60/40, m.p.~183° C.) solder [Technic, Inc., www.technic.com] was then electroplated into the hinge regions. The height of the hinges was approximately 16 µm. After the solder electrodeposition, the photoresist layers were stripped off with acetone, the remaining Cu seed and Cr adhesion layers were etched and the 2D-precursor template composed of metal frames connected with solder hinges was immersed in N-Methyl Pyrrolidone (NMP) [Sigma-Aldrich, www.sigma-aldrich.com] to dissolve the sacrificial PMMA layer and release the precursors from the wafer. Approximately 50 precursors in NMP were spread across a small crystallization dish and a small amount of #5 RMA flux [Indium Corporation, www.indium.com] was added to dissolve any solder oxides that may have formed. The dish was heated to 100° C. for 3 minutes and then ramped up to 250° C. for approximately 90 seconds until the solder became molten. During reflow, if the solder wet the top layer of metal on the 2D precursor, the fabrication yields were poor. Solder wet copper well but did not we Ni well, hence for containers with Cu frames it was necessary to add a thin Ni layer to improve yields. When solder reflowed, the molten solder at the hinges and generated the torque to fold the 2D precursors into 3D microcontainers. Upon cooling, the solder solidified and permanently held the container frames together.

Container Loading:

Two methods were used to load reagents into the containers, depending on the wettability of the chemical reagent on the container. When the chemical wet the container well, several boxes were simultaneously loaded by immersing them in a drop of the chemical reagent. The solvent was removed by evaporation. This left behind the polymer [Pluronic® F68, BASF, www.basf.com] soaked with the chemical reagent.

The second method utilized two three-axes Newport micromanipulators [Models 460A & M462, www.newport.com] to independently control the position of the microcontainer and the syringe [World Precision Instruments, Inc. Nanofil™ Syringe, www.wpiinc.com]. The syringe was outfitted with a 36-gauge needle [WPII 36 gauge Needle, www.wpiinc.com] to facilitate loading of the microcontainers.

Chemical Release & Reaction Specifics:

Red Dye Diffusion Experiment (FIG. 23a-b): Containers were loaded with a mixture composed of: 1.6 mL (0.261 g) FD&C Red 40 [McCormick & CO., Inc., www.mccormick.com] and an aqueous polymeric solution composed of 1.0 g of Pluronic F68 dissolved in 10 mL of water (18.4 M $\Omega$). A 2:1:2 (by volume) mixture of glycerol ethanol water was used as the diffusion medium and this medium was added to a small chamber containing the loaded microcontainer. The diffusion profiles were imaged using a stereozoom binocular microscope.

Magnetically-Guided Phenolphthalein-KOH Reaction (FIG. 23c): The indicator mixture for the phenolpthalien-KOH reaction was prepared by adding 0.25 mL of phenolphthalein solution (0.5 g of phenolphthalein [Frey Scientific, www.freyscientific.com] in 100 mL of 95% ethanol) to an aqueous polymeric solution composed of 1.0 g of Pluronic F68 dissolved in 10 mL water and loaded into a nickel-based microcontainer. The microcontainer was placed into a well of a tissue culture plate [Falcon® Multiwell™ Tissue Culture Plate, 24 Well, www.bdbiosciences.com], and a 1:1:1 (by volume) glycerol: water: 1M KOH (aq) medium was introduced into the chamber. The microcontainer was guided and controlled using a 0.35 pull lb., ⅛" diameter AlNiCo round bar magnet [McMaster-Carr, www.mcmaster.com].

Copper (II) Sulfate Pentahydrate-KOH Reaction (FIG. 24a-c):

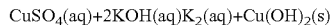

The copper sulfate reactant mixture was prepared by dissolving 1.0 g of Pluronic F68 into 10 mil of 0.5 M Cu(II)SO4 aqueous solution [Sigma-Aldrich, www.sigma-aldrich.com] and was loaded into a microcontainer. The potassium hydroxide reactant mixture was prepared by dissolving 1.0 g of Pluronic F68 into 10 mL of 1.0 M KOH(aq) and was loaded into a second microcontainer. The microcontainers were placed in close proximity into a poly (dimethyl siloxane) [PDMS, Dow Corning Sylgard® 184, www.dowcorning.com] microwell. The microwell was fabricated by molding PDMS against an SU-8 photoresist master. The diffusion and reaction medium was water.

Phenolphtalein-KOH Reaction (FIG. 24d-f): The indicator mixture for the phenolphthalein-KOH reaction was prepared by adding 0.25 mL of phenolphthalein solution to an aqueous polymeric solution composed of 1.0 g of Pluronic F68 dissolved 10 mL water. The alkaline mixture was prepared by adding 0.5 mL of 4M KOH(aq) [Sigma-Aldrich, www.sigma-aldrich.com] to an aqueous polymeric solution composed of 1.0 g Pluronic F68 and 10 mL water. Two containers were loaded with the phenolphthalein solution and one with the KOH solution. The three containers were then placed into a PDMS microwell, with water as the diffusion and reaction medium. The reactions were also imaged using a stereozoom binocular microscope.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter process, process step or steps, to the objective spirit and scope of the present invention. All such modifications are intended to be within the scope of the claims appended hereto.

What is claimed is:

1. A three-dimensional particle comprising a plurality of two-dimensional faces capable of self-folding to form a hollow interior, wherein a size of the particle is microscale or nanoscale, and wherein the plurality of two-dimensional faces comprise a folding hinge between two adjacent faces and a locking hinge on an edge of a two-dimensional face, wherein the folding hinge between two adjacent faces has a width that is about twice a width of the locking hinge on an edge, wherein the plurality of two-dimensional faces comprising the three-dimensional particle are permanently held together by solid hinges, and wherein the particle further comprises at least one of (i) an active electronic or semiconductor component; and (ii) at least one substance encapsulated within the particle.

2. The particle of claim 1, wherein the hinge comprises any liquefiable material.

3. The particle of claim 2, wherein the hinge is selected from the group consisting of a polymer, a gel, glass or a metal.

4. The particle of claim 1, wherein the particle has surfaces forming a polyhedral shape.

5. The particle of claim 4, wherein the shape is a cube.

6. The particle according to claim 1, wherein the two-dimensional faces are patterned with perforations or pores.

7. The particle according to claim 6, wherein the perforations or pores are created photolithographically, electrolytically, or by using electron beam lithography.

8. The particle according to claim 6, wherein the perforations or pores have a size from about 0.1 nm to about 1 cm.

9. The particle of claim 8, wherein the perforations or pores have a size from about 10 nm to about 1 cm.

10. The particle according to claim 1, wherein the particle is fabricated from at least one material selected from the group consisting of a metal, a polymer, a glass, a semiconductor, an insulator, and combinations thereof.

11. The particle according to claim 1, wherein the active electronic or semiconductor component is selected from the group consisting of transistors, sensors, actuators, light emitting diodes, photodiodes and solar cells.

12. The particle according to claim 10, wherein the metal is copper or nickel.

13. The particle according to claim 1, wherein the particle is a Faraday cage.

14. The particle according to claim 1, wherein the particle is coated with a biocompatible material.

15. The particle according, to claim 14, wherein the particle is associated with a biosensor.

16. The particle according to claim 14, wherein the biocompatible material is a metal, a polymer, or a combination thereof.

17. The particle according to claim 1, wherein the particle further comprises perforations or pores in the two-dimensional faces of the particle to allow release of the at least one substance encapsulated within the particle.

18. The particle of claim 1, wherein the substance is a therapeutic agent.

19. The particle according to claim 18, wherein the therapeutic agent is selected from the group consisting of a cell, a chemical or biological agent, a pharmaceutical agent, a composition, a tissue, a gel, and a polymer.

20. The particle according to claim 1, wherein the particle is administered to a subject and location of the particle in the subject is non-invasively tracked by magnetic resonance imaging (MRI) or CAT scan (CT).

21. The particle according to claim 20, wherein the particle is imaged with negative contrast relative to background or positive contrast relative to background.

22. The particle of claim 18, additionally comprising a radio frequency tag.

23. The particle of claim 22, wherein the substance may be released upon the particle's exposure to a pre-selected frequency.

24. The particle of claim 22, wherein the substance may be released upon the particle's exposure to electromagnetic radiation.

25. The particle of claim 24, wherein the electromagnetic radiation is triggered remotely.

26. The particle of claim 24, wherein the electromagnetic radiation ranges from 1 KHz to 1 Peta Hz.

27. The particle of claim 18, wherein the substance may be released upon the particle's exposure to inductive heating.

28. The particle of claim 27, wherein the inductive heating is triggered remotely.

29. The particle of claim 1, wherein the size of the particle ranges from 1 nm to 2 nm.

* * * * *